(12) United States Patent
Husher et al.

(10) Patent No.: US 11,300,485 B2
(45) Date of Patent: Apr. 12, 2022

(54) PROCESS RECORD SLIDE FOR STAINING AND METHOD OF USING THE SAME

(71) Applicant: ShenZhen PRS Limited, ShenZhen (CN)

(72) Inventors: Frederick Knute Husher, Melbourne Beach, FL (US); Jee Jong Shum, Miami, FL (US)

(73) Assignee: SHENZHEN PRS LIMITED, Shenzhen (CN)

( * ) Notice: Subject to any disclaimer, the term of this patent is extended or adjusted under 35 U.S.C. 154(b) by 0 days.

(21) Appl. No.: 17/147,139

(22) Filed: Jan. 12, 2021

(65) Prior Publication Data

US 2021/0131927 A1    May 6, 2021

Related U.S. Application Data

(63) Continuation of application No. 16/597,930, filed on Oct. 10, 2019, now Pat. No. 10,921,223.

(60) Provisional application No. 62/745,074, filed on Oct. 12, 2018.

(51) Int. Cl.
  *G01N 1/30*  (2006.01)
  *G01N 33/543*  (2006.01)
  *G01N 1/28*  (2006.01)

(52) U.S. Cl.
  CPC ......... *G01N 1/30* (2013.01); *G01N 33/54393* (2013.01); *G01N 2001/2893* (2013.01)

(58) Field of Classification Search
  None
  See application file for complete search history.

(56) References Cited

U.S. PATENT DOCUMENTS

| 7,271,008 | B2 | 9/2007 | Floyd |
| 10,921,223 | B2 * | 2/2021 | Husher ............... G02B 21/34 |
| 2005/0032129 | A1 | 2/2005 | Hasui |
| 2016/0274006 | A1 | 9/2016 | Sompuram et al. |

FOREIGN PATENT DOCUMENTS

| CN | 102435728 A | 5/2012 |
| CN | 103116018 A | 5/2013 |
| EP | 0266077 A1 | 5/1998 |
| WO | 2005003773 A1 | 1/2005 |
| WO | 2013043388 A1 | 3/2013 |
| WO | 2018228575 A1 | 12/2018 |

OTHER PUBLICATIONS

International search report dated Apr. 23, 2020 from corresponding application No. PCT/IB2019/058703.

(Continued)

*Primary Examiner* — Lisa M Caputo
*Assistant Examiner* — Nigel H Plumb
(74) *Attorney, Agent, or Firm* — Hauptman Ham, LLP

(57) ABSTRACT

Described herein is a process record slide for staining. The process record slide includes a detection area for mounting a sample and a control area including one or more control targets. Also described herein is a method of using the process record slide in an immunohistochemical (IHC) or an immunochemistry (ICC) staining process.

20 Claims, 13 Drawing Sheets

(56) References Cited

OTHER PUBLICATIONS

Westgard et al., "A Multi-Rule Shewhart Chart for Quality Control in Clinical Chemistry", Clinical Chemistry, 1981; vol. 27, No. 3, pp. 493-501.

Riera et al., "Use of Cultured Cells as a Control for Quantitative Immunocytochemical Analysis of Estrogen Receptor in Breast Cancer The Quicgel Method", American Society of Clinical Pathologists, 1999; 111:329-335.

International Preliminary Report on Patentability issued in corresponding International Application No. PCT/IB201/058703; dated Apr. 8, 2021; 6 pgs.

* cited by examiner

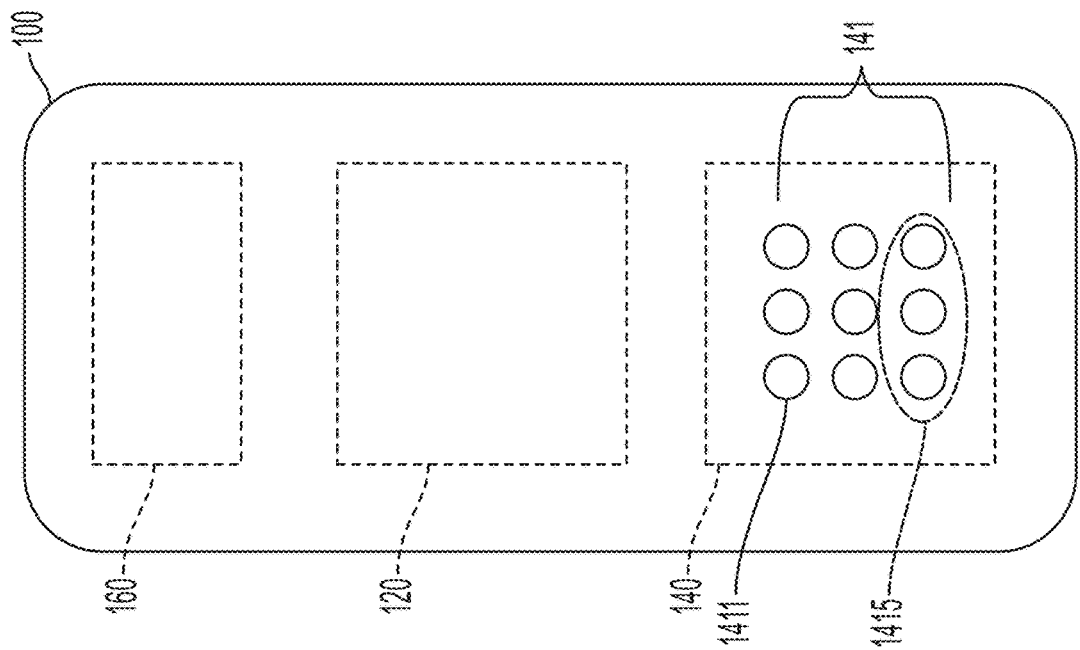

PROCESS RECORD SLIDE FOR STAINING AND METHOD OF USING THE SAME

PRIORITY CLAIM AND CROSS-REFERENCE

The instant application is a Continuation of U.S. patent application Ser. No. 16/597,930, filed Oct. 10, 2019, and claims priority from U.S. Provisional Application No. 62/745,074, filed Oct. 12, 2018, the entireties of which are hereby incorporated herein by their reference.

BACKGROUND

Immunohistochemistry methods as well as other immunochemical methods are multi-step procedures. These methods include a sequence of reagent exchanges, incubations, and washings. The procedures require skilled personnel and often the use of an automated staining machine. Results can vary significantly among laboratories or institutions because of non-uniformity, or lack of, in process quality control standards. Diagnostic interpretation of the processed slide relies on subjective analysis by a pathologist, who in most cases was not involved with the staining process.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 2 is a process record slide in accordance with some embodiments.

DETAILED DESCRIPTION

Figure 1:
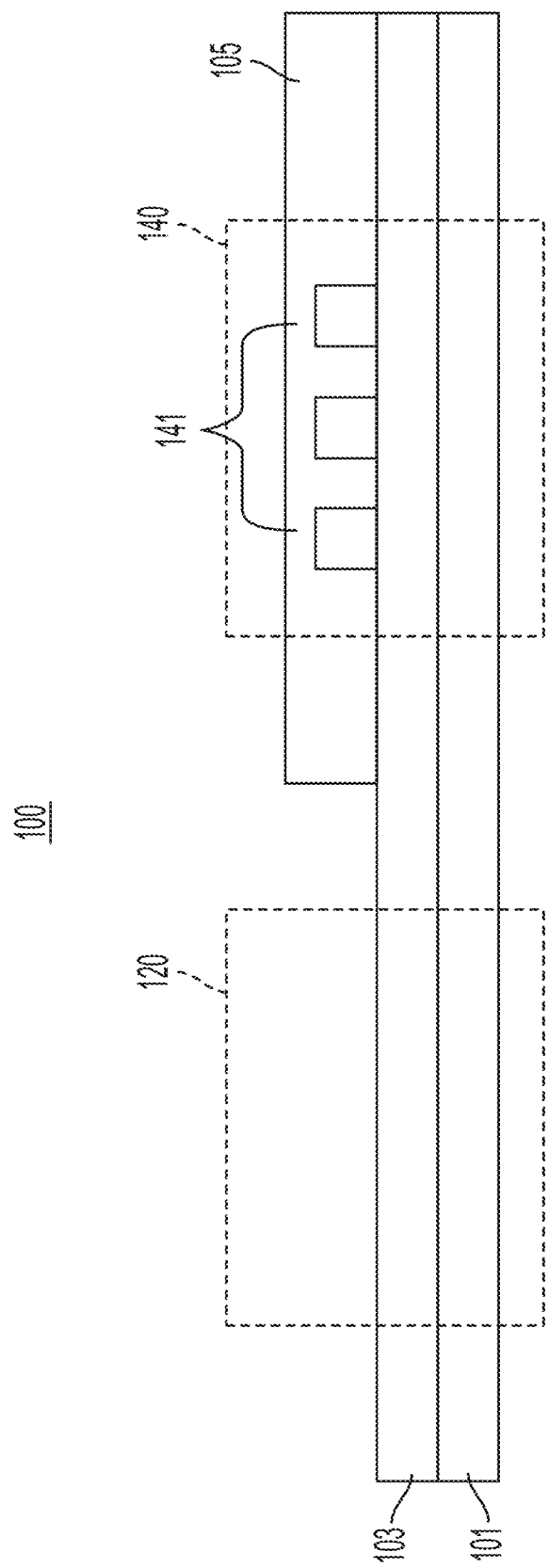
FIG. 1 is a process record slide in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

For immunohistochemistry methods and other immunochemical methods, both automated and manual procedures include steps where care should be excised. For example, care must be exercised to avoid the loss of or to damage the specimen on the slide. Since thorough washing of the specimen between reagent applications is used to remove any unbound antibody, as residues would be amplified, and excess liquid is removed to avoid carryover of the previous reagent and/or unwanted dilution of the subsequent reagent, yet specimens cannot be allowed to dry out. In addition, sufficient antibody reagents must be applied to cover the slide area, but waste needs to be kept to a minimum as the reagents are costly.

In addition, reagents used in immunohistochemical methods as well as immunochemical methods, such as enzyme solutions and peroxidase color development reagents, have limited stability at working temperature or at room temperature. The limited stability results in frequent preparation of the reagents. Furthermore, nonspecific antibody binding which leads to erroneous results remains a problem.

Immunohistochemical (IHC) staining in general, is used to assess the presence of specific antigen sites in a patient tissue section. In IHC assay, subjective interpretation is applied against the stain density on the tissue section to assign the diagnostic level of an abnormal or cancerous condition. An assumption is often made that the IHC processing functions correctly and that the tissue section would be marked with visible chromogen markers identifying the abnormal or cancerous conditions if the markers are present. However, failure of the antigen retrieval process or mistakes on the part of the lab technician or during the stain processes often leaves no identifiable artifacts. When this happens, the IHC assay provides nothing more than what would have been provided by a hematoxylin and eosin (H&E) staining. In addition, the failures or mistakes in the staining process sometimes leads to misdiagnosis, which affects the subsequent treatment.

Methods and reagents that improve results and minimize reagent preparation would facilitate both manual and automated immunohistochemical methods. Many of the improvements could be readily applied to related immunochemical methods such as enzyme-linked immunosorbent assays (ELISA), immunofluorescence assays and in situ hybridization.

Due to the above, completely eliminating errors in the immunohistochemistry methods and immunochemical methods is difficult. As such, various methods of revealing the existence and/or extent of the errors have been developed. Some of the methods as well as the limitations of the methods will be described below.

Reference may be made to "Use of cultured cells as a control for quantitative immunocytochemical analysis of estrogen receptor in breast cancer the Quicgel method" (the entirety of which is hereby incorporated herein by reference). This references states that the variation in tissue fixation, processing, and staining is largely responsible for poor reproducibility of estrogen receptor (ER) immunohistochemistry assays. A frozen, agar-suspended pellet of MCF-7 cells with known ER content was added to each of 55 samples of invasive breast carcinoma (IBC), serving as a control. Image analysis determined percentages of positive area (positive nuclei per total nuclei analyzed) and positive stain (sum of optical density of the positive nuclear area divided by sum of the optical density of all nuclei studied) of MCF-7 cells and IBC. MCF-7 cells had a mean value of 150 fmol/mg of ER by dextran-coated charcoal analysis. Image analysis of MCF-7 cells included with the 55 cases showed a mean positive area of 70.81. Positive staining from the IBC cases ranged from 0 to 98.5. By using the known ER content and the positive area of the MCF-7 cells, a conversion factor was used to translate the positive area of the clinical specimens to a femtomole equivalent, which for the 55 IBCs ranged from 0 to 1,790 (mean, 187). Inclusion of a control with known femtomole quantity of ER provides an internal standard for quality control and ER quantitation.

Reference may be made to CN102435728 (the entirety of which is hereby incorporated herein by reference). This reference describes a method of preparing and utilizing a positive control for inspecting and controlling the quality of immunohistochemical processes. According to CN102435728, a control target is constructed by adsorbing a polypeptide or a protein having specific reaction with an antibody on a slide at different concentrations. A sample tissue is then mounted on the slide and a conventional immunohistochemical process is performed on the slide. Because the sample tissue and the control targets undergo the same staining process, the staining result of the polypeptide/protein is indicative of the results of the immunohistochemical process on the tissue. CN102435728 also describes arranging the positive control protein or polypeptide on the immunohistochemical slide.

One of ordinary skill evaluating the method of CN102435728 would understand that the density of the protein/peptide in the control target is inconsistent. The reason is that binding of the peptide segments to the dextran polymer depends on viscosity of the mixing solution, washing process that removes excess peptides from the dextran, and temperature. In addition, the size of the precipitated polymer pellets varies with the bath concentration, the reaction temperature, and the NaOH injection.

One of ordinary skill evaluating the method of CN102435728 would understand that the building targets of known reactivity (stain density) is difficult. The reason is that the concentration of available peptides in the polymer pellets cannot be easily derived. As such, the resulted control is only a yes/no primary antibody detector.

One of ordinary skill evaluating the method of CN102435728 would understand that while the dextran is able to capture proteins for antibodies to target, the captured protein only provides a yes/no result. Thus, a baseline detection ruler cannot be established to support, e.g., a digital imaging.

One of ordinary skill evaluating the method of CN102435728 would understand that the proteins/peptides absorbed on the slide often leak during the antigen retrieval process. Due to the relatively small size of the slide and therefore the close proximity between the control targets and the sample area, the leaked proteins/peptides can move to the tissue section. As such, the leakage can bind to the co-resident tissue section and slide adhesive to cause non-specific staining.

Reference is made to Horizon Diagnostics, which provides slides constructed differently from those as described in CN102435728. In the slides of Horizon Diagnostics, the control targets are cultured cell lines. The cell lines are genetically engineered to include coding sequences of specific antigen peptides in the DNA. The genetically engineered cells are fixed in tissue blocks in the slide by formalin and paraffinized in the form of a loose cell slurry. In addition, control targets including non-reactive cells are also included in the slides as negative controls. To produce an array of control targets, each cell group are formed as a cylinder core aligned with other cores, and the entire array is cut as a single section for application to the slide. These cell lines can be replicated as desired and therefore considered as renewable.

One of ordinary skill evaluating the slides made by Horizon Diagnostics would understand that the control targets can only provide a yes/no result due to the uncontrollable density variations of the reactive antigens presented in the control targets. The reason is that controlling the amount of cells or the amount of antigens produced by the cells are difficult. As such, each control target includes different amounts of antigens. In addition, since the control targets go through the antigen retrieval process, which introduces another variable to the antigen amount in the control targets.

One of ordinary skill evaluating the slides made by Horizon Diagnostics would understand that the amount of antigen in each cell well cannot be controlled by simply mixing an antigen producing cell line and a blank cell line in certain ratios. The reason is that the electrostatic charge on the different cell lines are often different. As such, the different cell lines often dissociate during the cell culture process and grow into sections of different cells, making the generation of antigen density scale improbable or even impossible.

One of ordinary skill evaluating the slides made by Horizon Diagnostics would understand that there is inconsistent cell line performance since the cell reproduction has a limited replication life. There can be no assurances that a new cell line will have the same antigen density as any previous cell line.

One of ordinary skill evaluating the slides made by Horizon Diagnostics would understand that making the control target of Horizon Diagnostics is not cost effective due to the manual labor required to construct tissue blocks, section the blocks, and apply cut section to the slide.

Reference may be made to US2016/0274006A1 (the entirety of which is hereby incorporated herein by reference) which describes method and apparatus that serve as a control and calibrator for assays performed on cells and tissues mounted on a microscope slide. The apparatus of US2016/0274006A1 includes a quality control moiety, such as a peptide epitope, linked to a particulate object, such as a clear spherical bead and the bead is preferably approximately the size of a cell. The quality control moiety is designed to behave in a similar manner in the assay as an analyte, yielding a positive assay reaction. The bead is retained on a microscope slide during the steps of staining by a novel liquid matrix, which solidifies upon drying and causes adherence of the beads to the microscope slide.

This control and calibrator solution of US2016/0274006A1, however, has limited practicality. Because that the control target material is coated on beads and sparsely located, the stability of the targets tends to be weak and the target data is difficult to extract. In addition, when imaging a single bead, the stain color changes from the top center to the rim, thus introducing additional variables.

Reference may be made to U.S. Pat. No. 7,271,008B2 (the entirety of which is hereby incorporated herein by reference) which describes a device and methods for determining the quality of reagents used in an assay process, particularly a multistep immunohistochemical assay. In particular, the device comprises a substrate with a plurality of compounds affixed to a substrate, where each compound is reactive with a reagent used in the assay.

The device of U.S. Pat. No. 7,271,008B2 provides a quality control that evaluates the staining by the secondary antibody. However, the device of U.S. Pat. No. 7,271,008B2 does not undergo the same steps of an IHC staining together with the sample. Therefore, representativeness of the IHC staining by the device is limited. In addition, the device uses amino-silane in the substrate, which could not form covalent bonds that are capable of surviving the antigen retrieval processing. Also, the alkaline phosphatase target would breakdown upon exposure to the antigen retrieval temperatures. As such, the device of U.S. Pat. No. 7,271,008B2 is not useful in monitoring the antigen retrieval process, which is known to introduce unknown variables in the IHC staining process.

In view of the above, the instant specification, in some embodiments, describes a process record slide and a method for staining that addresses these issues. Specifically, the instant specification describes a process record slide that allows a patient sample and control targets to co-reside and experience the staining process together. As such, in the processing of the sample, the control targets are also stained, which reveals the existence and extent of processing error(s) as deviation against a known target baseline. One of ordinary skill in the art would recognize that changes in concentration of the staining reagents applied to a sample will impact subjective analysis. Excessive primary antibody often causes non-specific staining on the tissue section. Ignoring the antigen retrieval processing, the efficacy of the primary antibody, secondary antibody, and chromogen reagents will affect the stain color density (the indication of antigen density on the tissue section.) Aging of antibody proteins results in the hinge between the Fab and Fc domains breaking soon followed by splitting of the Fc domain. Only those antibodies containing both Fab and Fc domains will result in successful operation. Many of the chromogen reagents, containing the colorant for precipitation, have short lifetime behaviors, some as short as hours. As a result, chromogen reagents of different ages will have different performances leading to variations in stain color density. Thus, the performance of the reagents can and do impact the stain color density in the observed sample. Since the same stain reagents are used for both the sample and the control targets, variation in reagent age and amount is accounted for by the control targets in order to provide more objective information for analysis. According to these embodiments, the process record slides are able to deliver an effective Process QC with desirable accuracy and precision within a cost sensitive price point such that it can be used on every IHC and ICC slide.

Process Record Slide

In some embodiments, the instant specification is directed to a process record slide. In the instant specification, the term "process record slide" is alternatively referred to as a "slide", a "PRS" or a "PRS-IHC." The "IHC" portion in the term "PRS-IHC" is not meant to limit the construction or the function of the slide to immunohistochemcial (IHC) staining only. Rather, one of ordinary skill in the art would understand that the process record slide as described herein can be used in other staining processes, such as immunochemistry (ICC), as well.

In some embodiments, the instant specification is directed to a process record slide that allows easy determination of the efficacy of steps commonly involved in immunohistochemcial (IHC) or immunochemistry (ICC) assays. These steps include paraffin removal, antigen retrieval, primary staining, secondary staining and etc.

Refer to FIG. 1, in some embodiments, the process record slide 100 includes a substrate 101, an adhesive layer 103, and one or more control targets 141.

In some embodiments the substrate 101 includes a glass substrate, a plastic substrate or a polymer substrate.

In some embodiments, the adhesive layer 103 includes an adhesive. In some embodiments, the adhesive binds covalently to the substrate 101, such as a glass substrate.

In some embodiments, the adhesive provides a slightly hydrophilic surface on the slide. In some embodiments, a material of the adhesive includes an end group that is presented to biomaterials and is adjustable at the time of manufacturing for the surface wettability. In some embodiments, the end group includes one or more groups selected from the group consisting of —ROH, —R(C=O)OH, —RNH$_3$, —R(C=O)NH$_2$, and —RNH$_2$. In some embodiments, the adhesive layer 103 includes an adhesive that is the same as or similar to the adhesive found in the coatings of Thermo-Fisher SuperFrost slide GL4951P.

In some embodiments, the one or more control targets 141 are deposited on the substrate layer via the adhesive layer. In some embodiments, the one or more control targets are deposited in the control area 140 of the slide 100.

In some embodiments, the control targets 141 includes chemical compounds that react with one or more reagents used in the IHC or ICC process and produce a reading, such as a reading in the form of a color. Each of the control targets 141 includes a different concentration of chemical compounds. The variation in the concentration in the chemical compounds provides an identifiable difference between the control targets 141 following interaction with the one or more reagents in the IHC or ICC process.

In some embodiments, the process record slide 100 further includes a protective coating 105 covering an entirety or a portion of the slide 100. In some embodiments, the protective coating 105 seals the control targets 141 from the outside environment. As detailed below, the control targets 141 sometimes include proteins, peptides or other targets of biological origin. Therefore, the protective coating 105 protects the control targets 141 from oxidation or microbial attack.

In some embodiments, the protective coating 105 is a paraffin coating. According to these embodiments, the paraffin coating is removed together with the embedding paraffin on the tissue/cell sample to be studied by the IHC or ICC assay by the same de-paraffinization step.

Refer to FIGS. 1-3C, in some embodiments, the process record slide 100 includes a detection area 120 configured to hold a sample, and a control area 140.

In some embodiments, the detection area 120 is configured to hold a patient sample, such as a tissue section, or loose cells.

In some embodiments, the control area 140 holds one or more control targets 141 that undergo the staining process together with the sample held in the detection area.

In some embodiments, the detection area 120 and control area 140 have a marked boundary. In some embodiments, the detection area 120 and control area 140 do not have a marked boundary and are classified based on the respective function.

In some embodiments, the control targets 141 are arranged in the form of one or more control target loading dots 1411. In some embodiments, the loading dots are of a regular or an irregular shape. In some embodiments, the regular shapes including circles, ellipses, squares, or diamond shapes. In some embodiments, the control targets 141 are arranged in a 2D or a 3D configuration.

In some embodiments, the control targets 141 are arranged in the form of one or more control target arrays 1415, such as one or more arrays of control target loading dots 1411. In some embodiments, each of the control target arrays 1415 include one type of control targets that have the same or similar chemical and biochemical properties. In some embodiments, each of the control target arrays 1415 include one type of control targets that result in contrasting optical properties.

Figure 9:
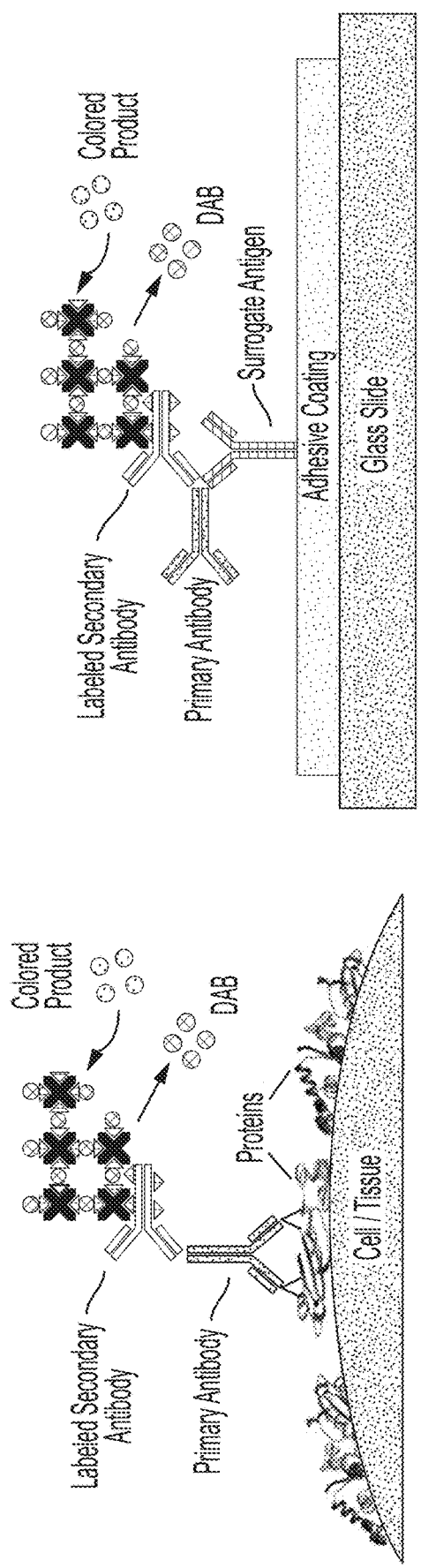
FIG. 9 is a staining process using a slide in accordance with some embodiments.

According to these embodiments, because the detection area 120 and the control area 140 are located on the same slide, during the IHC or ICC process, the samples held in the detection area 120 and the control targets 141 in the control area 140 undergoes the same staining steps (refer to FIG. 9). As such, the level of staining of the control targets 141 reveals the existence and extent of processing errors occurred during the IHC or ICC process, and the control targets 141 allow the processing errors of the IHC or ICC process to be analyzed as deviation against a known target baseline. Therefore, according to these embodiments, the process record slides are able to deliver an effective quality control with desirable accuracy and precision, with reduced subjective analysis, at a relatively low cost, resulting with an easy acceptance threshold. Furthermore, with subsequent digital image capture and processing, the stained control targets 141 can serve as an antigen density ruler, containing two scales: numerical antigen density and color density which can be applied to the co-resident sample to provide aid in, e.g., diagnostic determination.

In some embodiments, the control targets 141 are deposited on the slide in such manners that the control targets 141 are not significantly affected by the pretreatment steps commonly used in IHC or ICC staining. In some embodiments, the pretreatment steps include de-paraffinization or antigen retrieval. The pretreatment steps is described in below in detail.

In some embodiments, the slide 100 further includes a slide information area 160. In some embodiments, the slide information area 160 includes information on the type of the slide such as a lot number, date of manufacture, control target types, etc. Since the slide information, such as the information on control target types, is extensive, in some embodiments, the slide information area 160 includes a barcode recording the slide information. In some embodiments, the barcode includes a website link to a detailed description of the slide.

Figure 3C:
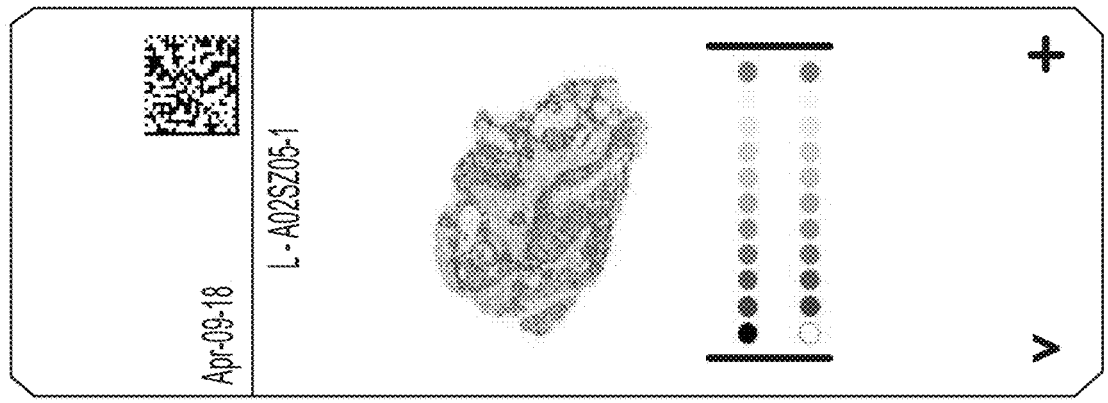
FIG. 3C is a process record slide after the staining process in accordance with some embodiments.
Figure 3B:
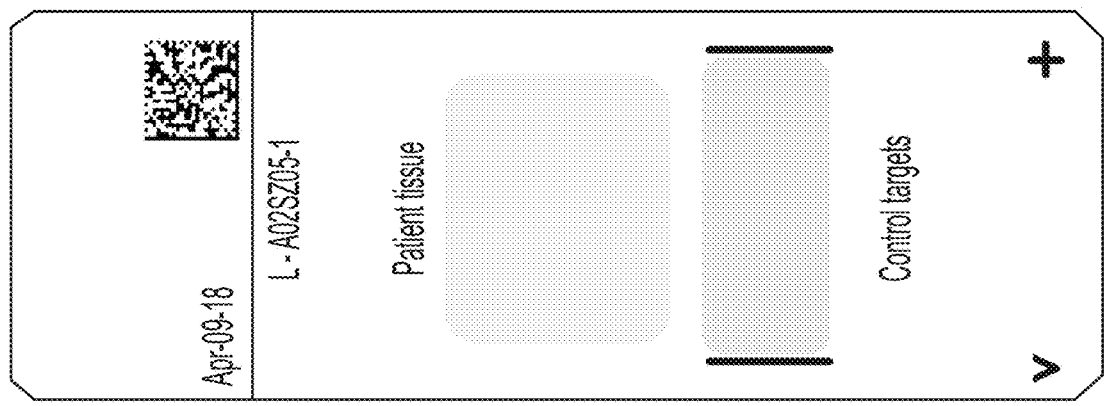
FIG. 3B is a process record slide after the manufacturing process is finished in accordance with some embodiments.
Figure 3A:
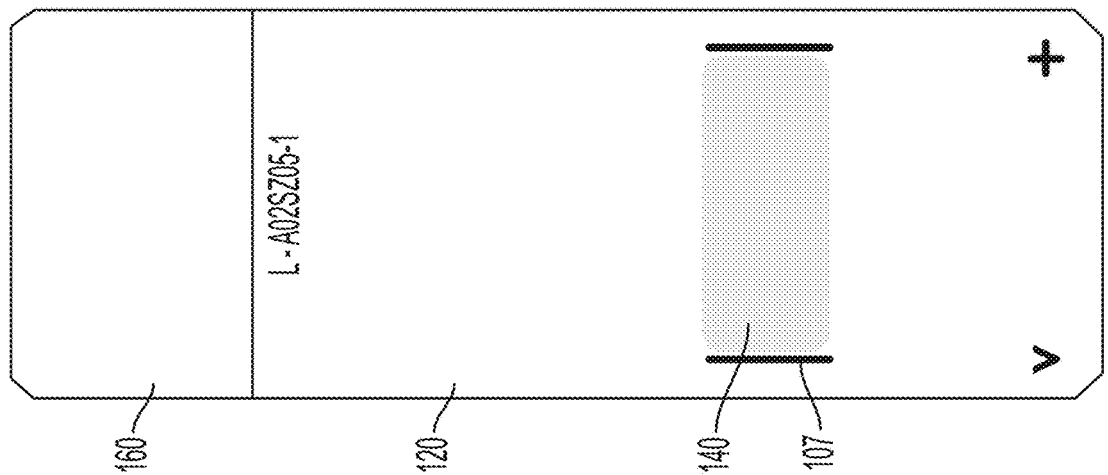
FIG. 3A is a process record slide during the manufacturing process in accordance with some embodiments.

Refer to FIG. 3, in some embodiments, the slide 100 further includes a bulging structure 107. According to these embodiments, the bulging structure 107 ensure that when stacked, the adjacent slide does not damage the paraffin coating or the control targets. In some embodiments, the bulging structure 107 includes a pair of bars or multiple dots extending beyond the control area 140. These bumpers help to the direct print ink-jet label printers commonly feed unmarked slides from the bottom of the magazine. Thus, the bumpers ensure that the paraffin coating and targets below are undamaged when one slide slides over another during the dispensing from the magazine.

Protective Coating

In some embodiments, the protective coating 105 is a paraffin coating.

Figure 4:
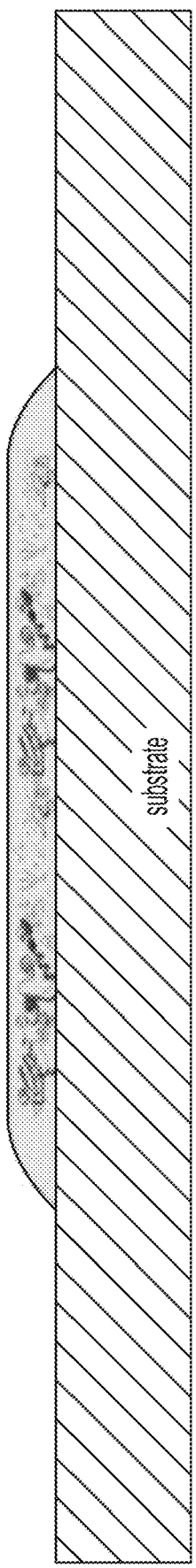
FIG. 4 is a process record slide including a paraffin coating in accordance with some embodiments.

Refer to FIG. 4, in some embodiments, the paraffin coating is a coating of paraffin wax on the control targets that seals the control targets.

Paraffin wax, in general, is a white or colorless soft solid, derived from petroleum, coal or oil shale, which consists of a mixture of hydrocarbon molecules containing between twenty and forty carbon atoms. It is solid at room temperature and begins to melt above approximately 37° C. (99° F.); its boiling point is >370° C. (698° F.). Common applications for paraffin wax include lubrication, electrical insulation, and candles; dyed paraffin wax can be made into crayons. It is distinct from kerosene and other petroleum products that are sometimes called paraffin.

In a pathology laboratory, water free paraffin wax is used to impregnate formaldehyde fixed tissue prior to sectioning thin samples of tissue. In this procedure, water is removed from the tissue through ascending strengths of alcohol (75% to absolute) and the tissue is cleared in an organic solvent such as xylene or one of the aliphatic substitutes, such as Xylol. The tissue is then placed in liquid paraffin wax for a period time in a vacuum oven to ensure that all air is extracted and then set in a mold block frame with liquid wax to cool and solidify. The sections are then cut on a microtome.

Embedding tissue sections into paraffin is a practice for the preservation of the biopsy tissues for a prolonged period of time. However, to the best knowledge of the instant inventors, the application of paraffin as a coating layer on a selected area of a microscope slide has not been reported.

As described below, control targets slide includes peptides or proteins, and therefore present a rich food source for bacteria or fungi. The peptides and proteins, as well as the antigen sites thereof (e.g. epitopes) are susceptible to oxidation which sometimes compromises the ability to bind antibodies. In addition, of the subsequent reaction involves hydroxyl groups, which can be damaged through reactions with airborne acids and bases. As such, slides containing protein deposits are often required to be stored at temperatures below what supports microbial growth, and need to be packaged in vacuum sealed. Unprotected slides, such as those exposed to environment, have shelf lives as short as 2 to 5 days depending upon ambient temperature, humidity, and airborne contaminate levels. Such are a constraint that limits the effective utilization of deposits.

Paraffin has anti-fungal and antibacterial capability and prevents oxidation of materials sealed under. The instant inventor has found that the paraffin coating extends viable life of the biomaterials from 3-5 days to 1-2 years, thereby significantly increases the shelf life of the process record slide.

Removal of the embedding paraffin from the sample is commonly performed during IHC or ICC stainings (this process is referred to as "de-paraffinization"). Therefore, in some embodiments, a formulation of the paraffin included in the protective layer 105 is the same as or similar to the formulation of the paraffin used in the embedding process.

As such, the paraffin coating can be removed at the same time of the de-paraffinization, thereby simplifying the staining process.

In some embodiments, paraffin is liquefied, applied on the slide and solidified, thereby forming the paraffin coating.

In some embodiments, the paraffin is blended with a solvent to change the material state from solid to liquid at room temperatures. In some embodiments, the solvent includes, Xylene or an Aliphatic solvent, for example Xylol. The blending with the solvent reduces the viscosity and slows down solidification following deposition. In some embodiments, the solvent includes toluene, paint thinner, turpentine, or a 50:50 mix of acetone & kerosene. Paraplast X-tra additionally includes butylated hydroxytoluene, a phenolic antioxidant, further reducing the oxidation degradation of protein, peptide, or inorganic targets.

In some embodiments, the solid paraffin is melted at a temperature of no more than 75° C. above the paraffin melt temperature. The melted paraffin is then slowly added with an aliphatic solvent until the saturation point is observed (i.e., solids are formed). The mixture is allowed to cool to about 45° C. Additional aliphatic solvent is then added until the mixture is completely clear.

In some embodiments, the paraffin coating is applied over biomaterial and special stain reactive deposits previously deposited to a microscope slide. The biomaterials, as described below, include proteins, peptides, conjugated proteins, protein coated beads, peptide coated beads, conjugated coated beads, special stain reactive end groups that uniquely capture a stain material, and etc.

In some embodiments, the paraffin is applied onto the slide by spraying, inkjet deposition, transfer printing such as pad printing, screen printing, and vapor deposition. In some embodiments, the paraffin coating is applied onto the slide by heating to melt and/or blend paraffin particles into a monolithic surface coating sealing both the control targets and a slide surface surrounding the control targets.

In some embodiments, after the paraffin coating is applied onto the slide, the slide is heated to drive off the solvent from the paraffin, thereby ensuring that the paraffin returns to a hardened state. A process for removing the solvent is performed by infrared light applied from the paraffin wax side of the slide. This method preferentially targets the solvent over the paraffin or biomaterials that are below the paraffin, thereby minimizing the needed thermal energy. The evaporated solvent is free to leave the paraffin without impediment.

In some embodiments, the paraffin is a blend of purified paraffin, synthetic polymers, and other materials. In some embodiments, desirable melting temperature, hardness, and viscosity of the paraffin is obtained by experimenting on ratios of the components. However, for the purposes of protecting biomaterials the paraffin is purified and water free.

In some embodiments, the paraffin coating has a thickness of 5 microns or less.

In some embodiments, the paraffin in the protective coating 105 has a melting temperature of less than 60° C., such as less than 56° C.

In some embodiments, the paraffin is dissolvable by xylene, xylol, or an aliphatic replacement thereof.

In some embodiments, the paraffin formulation includes, but limited to, TissuePrep & TissuePrep 2 by Thermo Fisher, melting temp 56° C., Paraplast & Paraplast Plus by Leica, melting temp 56° C., and Paraplast X-tra by Leica, melting temp 50-54° C. In some embodiments the ambient temperature hardness of the paraffin coating is chosen to be the hardest formulation available with butylated hydroxytoluene added if not already in the formulation.

Primary Targets and Primary Target Arrays

In some embodiments, the control targets 141 include one or more primary targets to test primary antibody reagents.

As used herein, the term "primary targets" means a composition of reactive and non-reactive elements that specifically bind to a primary antibody by only one of its FcyR1 sites. As used herein, the term "primary protein" means a protein that binds to the FcyRI of the primary antibody. As used herein, the term "primary dummy protein" means a protein that will not react to any primary antibody or secondary antibodies. As used herein, the term "maximum target density" refers to the maximum monolayer density of adjacent proteins. As used herein, the term "surrogate antigen" refers to a protein that is not targeted by the primary antibody used in the IHC or the ICC assay, but nonetheless binds to the primary antibody via, for example, only one of the two FcyRI regions of the primary antibody (mouse or rabbit based) used in the IHC or the ICC assay. As used herein, the term "mouse only surrogate antigen" means a protein or antigen that uniquely reacts to only to the FcyRI of mouse based primary antibody. As used herein, the term "rabbit only surrogate antigen" means a peptide or protein that uniquely reacts to only the FcyR1 of a rabbit based primary antibody.

Placenta mammal proteins range between 50-65 kDa in weight. Primary antibody IgG proteins are composed of two Fab and one Fc domains that are usually modeled with a Y-shape. The Fc is joined to the two Fab domains by a hinge. All non-conjugated antibodies are grown within a host mammal (most often Mouse or Rabbit) through inoculation of the host by an antagonist antigen peptide. The host produces antibodies to fight off the offending antagonist antigen peptide by assembling a binding amino acid sequence near the N-terminal end of the antibody's Fab domain that can capture the mating antigen. The Fc domain of the antibody is always that of the host mammal. The Fc domain of the host antibody typically has three binding sites available to the secondary antibody in rank order of highest binding affinity to lowest: FcyRI (CD64), FcyRII (CD32), and FcyRIII (CD16).

The primary dummy protein is chosen to be unreactive to mouse, rabbit, goat, bovine, and sheep as these can often bind to the secondary antibody. In some embodiments, the dummy primary protein is any member of the Equine family: horse, donkey, zebra, taper, or rhino. BSA (bovine serum albumin) is not a suitable protein as BSA will not bind covalently to the tissue or most slide adhesive chemistries without heat and time. Bovine, sheep, and goat are also not suitable dummy proteins as in some cases these proteins may be confused with mouse or rabbit depending on the specificity of the primary antibody.

The primary protein is either host anti-mouse or host anti-rabbit. The host is limited to goat or any member of the equine family.

Primary proteins based on peptides can also be composed of mouse or rabbit FcyRI reactive peptides with cysteine residues at the C-terminal end covalently attached to a carrier protein such as KLH subunit (keyhole limpet hemocyanin). The KLH subunit is activated with Sulfo-SMCC at its free amine sites, which through conjugation binds to the cysteine residue of the peptide. Un-activated KLH subunit alone suffices to make the primary dummy protein.

It is important to note that KLH as a full protein is approximately 8000 kDa. In the full protein state, it is not stable in regards to pH or temperature, which will cause the protein to separate into subunits: KLH1 at 390 kDa and KLH2 @ 350 kDa. Either of these subunits can be used as carrier proteins, when Sulfo-SMCC activated, for peptides with a cysteine residue, usually at the C-terminal end of the peptide.

Figure 5B:
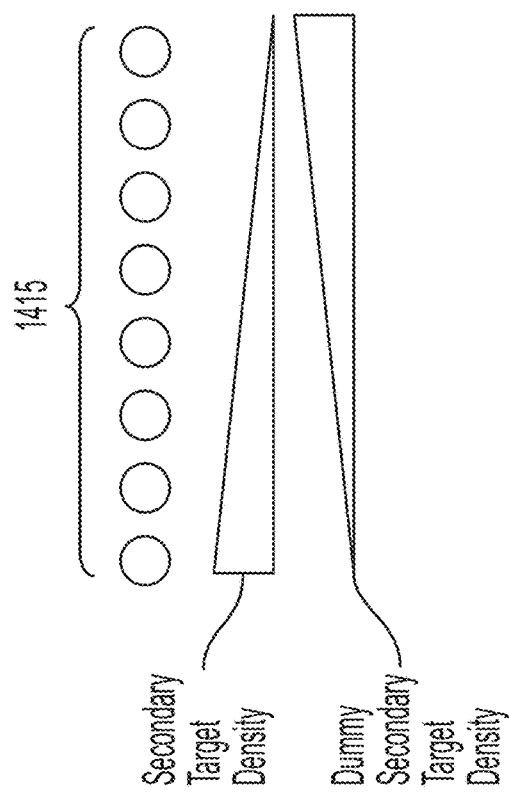
FIG. 5A and FIG. 5B are a primary target density gradient array and a secondary target density array of the slide in accordance with some embodiments.
Figure 5A:
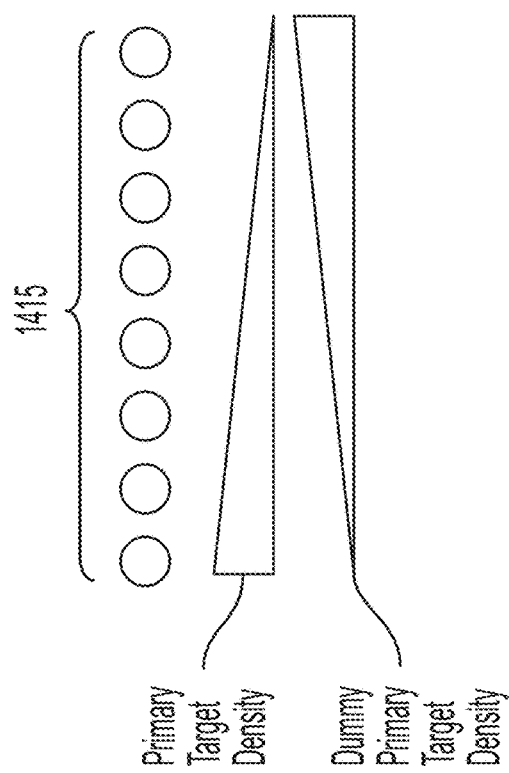

Refer to FIG. 5A, in some embodiments, the primary targets are arranged into a primary target array 1415. In some embodiments, the primary target array 1415 is a primary target density gradient array. Each target within the array must have the same maximum target density (proteins/surface area). However, the ratio between primary and dummy primary proteins are stepped in ratio to ensure that a wide range of primary antibody dilutions can be identified. As a general rule, detection by two primary surrogate antigen targets is sufficient to map the concentration to the detection transfer curve. In some embodiments, the primary target density gradient array includes a plurality of primary target loading dots wherein one array is mouse based and the other rabbit based.

In some embodiments, the density of the primary targets increases or decreases in a linear manner, such as 100%, 80%, 60%, 40%, etc. In some embodiments, the density of the primary targets increases or decreases in a logarithm manner, such as 100%, 33%, 10%, 3%, etc.

In some embodiments, in a primary target density gradient array, in the loading dot having the highest primary target density, the primary target density is sufficiently high so that the primary target is not able to saturate the loading dot during the staining process.

In some embodiments, the universal surrogate antigen is either Protein A or Protein G. Protein A binds to the FcγRI and to some areas within the Fab domain of placenta mammals. Protein G will bind only to the FcγRI site of most placenta mammals.

In some embodiments, the surrogate antigen must have specificity to mouse or rabbit only. To support the specificity, the surrogate antigen can be composed of anti-mouse and anti-rabbit proteins, anti-mouse and anti-rabbit peptides on a carrier protein, or anti-mouse and anti-rabbit VHH protein domains all respectively.

In some embodiments, the dummy surrogate antigen includes an antibody from an animal of the equine family or a hoofed placenta mammal except goat. Equine family includes animals such as horses, donkeys, tapirs, rhinos and mules. The equine family are evolutionarily and genetically further apart thus reducing the occurrence of non-specific staining. Goat cannot be used as often the secondary stain uses an anti-goat protein in its sequencing, which would bind to any unreacted goat primary sites.

Although the manner of interaction between the surrogate antigen and the primary antibody used in the staining process is different from those between the actual antigen and the primary antibody, the surrogate antigen targets can provide a valuation of the primary antibody's efficacy. The primary antibody comes with an assay of the concentration in mg/ml. However, the assay does not indicate what percentage of the assay represents complete IgG proteins. Since the density concentrations of the surrogate antigen in the targets are known the capture of the applied primary antibody concentration can be determined. By extrapolation the antigen density of the co-resident tissue section can be determined. The resolvability of antigen density on the tissue is limited to the cumulative displacement by the primary antibody (monoclonal or polyclonal), secondary antibody and enzyme gain of the secondary stain. The concentration of the applied primary antibody is dependent upon the tissue type and always has some excess margin included. Thus, the assumption is that the primary antibody will bind to all the available antigen sites within its displacement limitations.

In some embodiments, the primary target density gradient array is a loading dot array of a universal surrogate antigen. In some embodiments, the loading dots in the array includes increasing or decreasing density of the surrogate antigen. In some embodiments, the surrogate antigen is blended with one or more dummy proteins, such as dummy surrogate antibodies, and the increasing or decreasing concentration of the surrogate antigen is achieved by altering the ratio between the surrogate antigen and the dummy protein while maintaining the maximum target density.

In some embodiments, the control area 140 includes at least two arrays of surrogate antigen target. In some embodiments, the control area 140 includes a first surrogate antigen target array including an anti-mouse antibody and a second surrogate antigen target array including an anti-rabbit antibody, both blended with a dummy surrogate antigen to form the desired reactive density while maintaining the maximum target density.

Therefore, according to these embodiments, with the IHC or ICC steps the surrogate antigen primary targets can evaluate the primary antibody concentration using the enzyme gain and antigen retrieval factors developed by the secondary targets.

Antigen Retrieval Targets

In some embodiments, the control area 140 includes an antigen retrieval target.

IHC and ICC staining assays often include an antigen retrieval (also referred to as "AR") process. AR process can be performed with a heat induced epitope retrieval (HIER) method, or warm water antigen retrieval method. Depending on the method used as well as the implementation of the specific methods, significant amount of variation is introduced and the results varies from practitioner-to- practitioner and slide-to-slide. Direct measurement of the AR buffer and the buffer temperature is often not accurate. However, without a proper control, practitioners often have to assume blindly that the temperature and conditions of the AR buffer are ideal. Therefore, the lack of control often results in failures of the AR process to slip into the final evaluation, resulting in misjudgments.

The most common issues in the AR process is under recovery or over recovery of antigens. The under recovery condition occurs when the AR temperature is too low, exposure time is insufficient, etc. The over recovered condition occurs when the AR temperature is too high, the exposure to AR condition is too long, or the AR buffer condition is too harsh (e.g., >pH 9.5 or <pH 5.5.)

Therefore, in some embodiments, the antigen retrieval target is configured to provide indication on under recovery, nominal recovery, and over recovery during the AR process.

In some embodiments, the control area 140 includes a 3D AR target (ARM3D) and a 2D target (ARM2D). 2D and 3D targets are described in detail in the section below.

In some embodiments, the ARM2D target includes a 50:50 mix of mouse and rabbit protein (or protein from other species) at 100% concentration with minimal formaldehyde fixation. In some embodiments, the protein is IgG. Because 2D targets generates less signal than corresponding 3D targets, and the ARM2D target has minimal fixation, staining of the ARM2D target indicates an insufficient antigen retrieval.

In some embodiments, the ARM3D target includes a 50:50 mix of mouse and rabbit protein (or protein from other species) at 100% concentration deposited in a 3D scaffold that has been over fixed with formaldehyde. Because 3D targets generate more signal than corresponding 2D targets, and the ARM3D target is over fixed, the absence of staining of ARM3D target indicates that the AR process was too aggressive.

In some embodiments, the antigen retrieval target further includes a primary target gradient array or a secondary target gradient array in addition to the ARM2D or the ARM3D targets. In some embodiments, the primary target array or the secondary target array is the same as or similar to those as described above.

In some embodiments, the secondary target gradient array is a mouse or rabbit density gradient array. According to these embodiments, when 10% to no more than the 30% target dots of the mouse and rabbit gradient density arrays do not show visible staining, nominal recovered condition is indicated. The degree of AR process can then be assessed by the number of low concentration secondary targets that are not stained.

2D/3D Targets

In some embodiments, the control targets, such as the primary target, the secondary target or the antigen retrieval targets include a 2D target.

As used herein, the term "2D target" means that the peptide, protein, antigen, antibody or any other control target materials are deposited on a 2D plane on the slide.

2D targets are easier to deposit and are therefore relatively cheap to manufacture. Therefore, 2D targets are used when cost is concerned.

In some embodiments, the control targets, such as the primary target, the second target or the antigen retrieval targets include a 3D target.

As used herein, the term "3D target" means that at least one of the peptide, protein, antigen, antibody or any other control target materials are applied to a support structure and the composite deposited in a 3D space on the slide.

In one or more embodiments, 3D targets are constructed by forming a 3D scaffold on the slide, and depositing the control target materials on the scaffold. In some embodiments, the 3D scaffold is a polysaccharide cluster. The polysaccharides form covalent bonds with the hydroxyl or amine groups on peptides or on the surface of the protein, which links proteins together and anchors the target to the slide coating adhesive. In some embodiments, the control targets are fixed on the 3D scaffold by formaldehyde fixation. The target is then composed of both 2D and 3D components.

In one or more embodiments, the 3D targets are constructed from submicron beads to which the primary or secondary target materials are covalently bound. Formaldehyde fixation is then applied to stabilize the primary or secondary target materials against normal antigen retrieval processing. The deposited target then consists of 2D and 3D components.

Comparing to 2D targets, 3D targets behaves more similar to the staining samples. Staining samples of IHC or ICC, such as tissue sections and cells, have heights. The height of the samples commonly ranges from 4 microns to 10 microns. Antigen sites targeted in the staining can be anywhere on the exposed surface topology of the tissue section. As such, antigen sites in the sample can be planar at either top of bottom surface of the section or anywhere along a sidewall of the tissue. Thus, the antigen on the sidewall of the sample is able to precipitate significantly more colorant from the chromogen than the 2D targets are able to. The inclusion of the 3D elements with the 2D elements creates a step offset that can be applied to the other 2D target dots to form a virtual 3D array. Experimentally, it was found that any 3D target greater than 0.5 micron would stain as darkly as the tissue section.

In addition, DAB, a reagent commonly used in the staining process, ages over a relatively short amount of time resulting the changes of color and intensity. The instant inventors have found that in the DAB stained 3D targets the color and intensity changes in a manner similar to those in the sample.

Special Stains

In some embodiments, the control targets includes a special stain.

In some embodiments, the special stain includes Alcian Blue, Analine Blue—Orange G Solution, Azan Stain, Bielschowsky silver stain, Brow & Benn—Gramm Stain, Cresyl Violet, DAB, Fontana Masson, Gordon and Sweet's silver staining, Grocett's Methanamine silver method, Hall's Bilirubin stain, Jones Methanamine silver method, Luxol Fast Blue, Luxol Fast Blue—Cresyl Violet, Mucicarmine (Mayer's Method), Muller-Mowry colloidal Iron, Orange G, Nuclear Fast Red, PAS with Diastase Digestion, Periodic Acid Schiff (PAS), Phosphotungstic Acid, Haematoxylin, Picro Sirius Red, Toluidine Blue Acidified, Trichrome Gomoris One-Step, Trichrome—Masson's, Victoria Blue, Von Kossa, Weigert's Resorcin Fuchsin, Weigert's Iron Haematoxylin, Zell—Neelsen Method, or combinations thereof.

Imaging Reference Target

In some embodiments, the control area 140 further includes an imagining reference target. In some embodiments, the image target includes a black target or targets, a white target or targets, or a clear target.

Digital imaging of microscope slides containing stained biomaterials is evolving to perform prescreening and potentially full diagnostic determination on the stained materials. In some embodiments, after the staining process, the slide is subject to an imaging process during which the light illumination level or exposure are adjusted so that the digital image is not in compression at either the white or black boundary. In another approach black and white targets are located where the label is expected to be positioned. The underlying assumption is that the white and black targets represent the extremes that the level of staining signals can reach. However, in doing so there is compression in the digital scale as the black is much blacker and the white much whiter than can realized by the staining of a tissue section.

In some embodiments, the imaging reference target is printed on the slide. In some embodiments, the imaging reference target include a pair of the black target and the white target. In some embodiments, imaging reference targets are printed paint deposits which are non-reactive to the reagents used in the staining process.

Figure 12:
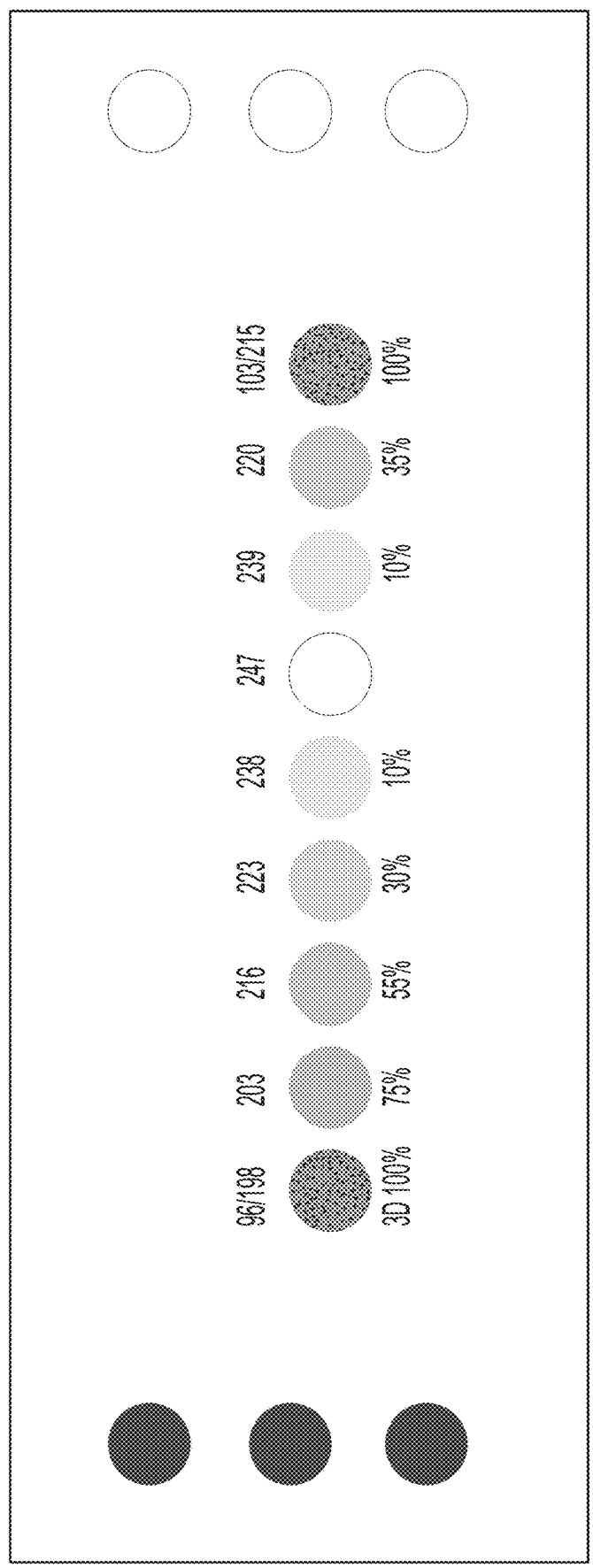
FIG. 12 is a single primary antibody control slide that works with any mouse or rabbit based primary antibody in accordance with some embodiments.

In some imaging systems, only transmitted light is used (illumination from the bottom of the slide). In other imaging systems, both transmitted light and reflected light (illumination from the top side of the slide). A third clear reference target supports reflected light illumination. Thus, for transmitted light illumination the black/white references are the black pigment target and the clear target respectively, while for reflected light illumination the black/white references are the clear target and white target respectfully. See FIG. 12 for an example of the single antibody slide and FIG. 13 for a dual antibody slide. The black/white targets are actually a string of dots, could alternatively be a bar that serve an additional function as bumpers to protect the target dots from damage when the slide is dispensed in an inkjet printer. Inkjet printers dispense slides from the bottom of the magazine. The bumpers ensure that the remaining stack of slides cannot scrape the paraffin coating or targets on the slide. These same bumps also ensure that should the slides be shipped in a packed form that the paraffin layer will not adhere to the bottom of an adjacent slide.

Imaging with transmitted light results in a misrepresentation of the antigen density on the tissue. This occurs because the stained tissue is not a monolithic slab where all antigen sites are on a single plane. Rather, the tissue can have antigen sites anywhere within its thickness. The secondary stain produces colorant particles that continue to precipitate until the particles cover the enzyme site and block continued precipitation. Should an antigen site be on the sidewall of the tissue section, the enzyme will never become covered and the precipitation will over express the antigen presence. With transmitted light the 'darkness' occurs because the precipitated colorant is thicker. In contrast, reflected light only 'sees' the top surface of the colorant pile resulting in a more accurate representation of antigen density.

In some embodiments, the white target has a color close to perfect white. Because a perfect white color is difficult to obtain, in some embodiments, the color of the white target is 5-10% away from perfect white. White colors less than 5% away from perfect white is difficult to produce, and colors more than 10% away from perfect white are sometimes not accurate enough as a control for staining signal strength.

In some embodiments, the white target includes a white pigment. In some embodiments, the white pigment is a metal oxide or a metal sulfate pigment that is stable with the passage of time when not left exposed to strong light. In some embodiments, the white pigment includes aluminum oxide, titanium oxide, or barium sulfate. In some embodiments, the metal oxide or the metal sulfate are in the form of beads.

In some embodiments, the black target includes a black pigment. In some embodiments, the black pigment includes a carbon based pigment. In some embodiments, the black pigment includes a carbon dust. In some embodiments, a diameter of the carbon dust is less than 2 microns.

In some embodiments, the imaging reference target includes an anhydride-based epoxy. In some embodiments, the imaging reference targets are produced by mixing pigments with the anhydride-based epoxy, and curing the anhydride based epoxy. Matching of the epoxy binder and the pigment are not particularly limited, a long as there is a good wetting between the pigment and the epoxy binder.

In some embodiments, the anhydride based epoxy includes an anhydride catalyzer that is able to eliminate unreacted amines of an amino-silane based catalyzer. Free amine groups capture both biomaterials and some of the staining reagents. As such free amine causes non-specific staining in the IHC and ICC process. Thus, the elimination of unreacted amines reduces non-specific staining.

In some embodiments, the anhydride-based epoxy paint includes an anhydride catalyzer, such as methyl tetrahydrophthalic anhydride or diphenyliodonium hexafluroroarsenate.

In some embodiments, curing the anhydride-based epoxy including subjecting the anhydride-based epoxy to a UV light, such as a UV light including a wavelength of 365 nm. In some embodiments, curing the anhydride-based epoxy paint further includes subjecting the anhydride based epoxy paint to heat, thereby allowing the epoxy to cross-link. The UV initiated anhydride-based epoxy and companion reagents thereof are not particularly limited. One of ordinary skill in the art is able to identify desirable anhydride-based epoxy by performing a search of products by anhydride producing companies.

In some embodiments, the imaging reference targets including the anhydride-based epoxy is deposited on the slide prior to the deposition of the primary targets, the second targets, or the antigen retrieval targets. The reason is that the heat treatment in the curing process of the anhydride-based epoxy can damage biomaterials included in the primary targets, the second targets, or the antigen retrieval targets. In some embodiments, the anhydride-based epoxy is cured by UV, and the deposition of the imaging reference targets can happen after deposition of the primary targets, the second targets, or the antigen retrieval targets as UV is less likely to damage peptides and proteins.

In some embodiments, the imaging reference target formulation is free of a surfactant, thereby preventing the ink/paint to be reactive to the range of stains and reagents these slides can experience.

In some embodiments, the imaging reference target is printed on the slide by a pad stamp. In other embodiments, the imaging reference target is printed by a syringe, because the syringe is able to control a size of target deposition.

Using the imaging reference targets, digital analysis is optimized because the all of the digitization range is within the slides definition of black/white versus the use of perfect black and white references. The digital analysis assists with interpolation of a color of the control targets in order to more precisely determine an amount of antigen present in the stained sample. The image reference target is used in order to assist with calibration of the digital analysis in order to provide a reference point for measuring an amount of reaction at the control targets.

Method of Depositing Control Targets

In some embodiments, the instant specification is directed to a method of depositing control targets on a process recording slide. In some embodiments, the slide and the control targets are the same as or similar to those as described above.

In some embodiments, the method of depositing control targets including depositing a primary control target or a secondary control target on the slide.

In some embodiments, depositing the primary control target or the secondary control target includes: preparing a solution of the control target at a predetermined concentration; fixing the control target; and printing the solution onto the slide.

In some embodiments, preparing the solution of the control target includes preparing a solution including the control target and a polysaccharide to function as the linker between the proteins and the slide adhesive.

In some embodiments, fixing the control target includes fixing the control target with formaldehyde. The formaldehyde crosslinks the control targets so that the control targets can withstand normal antigen retrieval protocols.

In some embodiments, the control targets are crosslinked. Within tissue, proteins are bound to other parts of the tissue that tend to keep the proteins from diffusion and denaturation. Since the control targets in the solution includes loose proteins, the control targets are more sensitive to heat and pH and, as such, tend to diffuse and denature on the slide, especially when going through the AR process in IHC or OCC.

In some embodiments, the primary targets are prepared as follows:

Form a set of the primary protein master dilutions of 1 ml with a concentration of 45 ug/ml. Dilute the Donkeyanti-Mouse, Donkey-anti-Rabbit, and Donkey IgG (H&L) proteins with dH2O as needed to realize the 45 ug/ml concentration. Typically, these proteins are between 1 and 10 mg/ml in concentration as purchased. Add in 10 ul of Thimersol as a fungal growth inhibitor.

Fix each master dilution with 10 ul 0.2% formaldehyde for 1-4hrs at 40-60° C.

Add in 30 ul of 0.45% concentration amylose as a linear polymer(has Thimersol added as a fungal growth inhibitor) and mix for 30-min Add in 20 ul of 0.1M ammonium bicarbonate to quench any unreacted formaldehyde Use the master protein solutions to form the target mixtures of Mouse with Donkey and Rabbit with Donkey, wherein each target contains 700 ul of the master protein solutions.

In some embodiments, the secondary targets are prepared as follows:

Form a set of the secondary protein master dilutions of 1 ml with a concentration of 45 ug/ml. Dilute the Mouse, Rabbit, and Donkey IgG (H&L) proteins with dH2O as needed to realize the 45 ug/ml concentration. Typically, these proteins are between 10 and 60 mg/ml in concentration as purchased. Add in 10 ul of Thimersol as a fungal growth inhibitor.

Fix each master dilution with 10 ul 0.2% formaldehyde for 1-4hrs at 40-50° C.

Add in 30 ul of 0.45% concentration amylose as a linear polymer (has Thimersol added as a fungal growth inhibitor) and mix for 30-min Add in 20 ul of 0.1M ammonium bicarbonate to quench any unreacted formaldehyde Use the master protein solutions to form the target mixtures of Mouse with Donkey and Rabbit with Donkey, wherein each target contains 700 ul of the master protein solutions.

In some embodiments, the prepared primary or secondary targets, or image reference targets are printed onto the slide in one print cycle according to the follows:

Print the target solutions onto an adhesive coated microscope

Air dry at 60° C. until all water has been evaporated then cool

Apply the paraffin-solvent mixture by spray over the printed target arrays

Reflow the paraffin to complete sealing of the targets arrays and drive off the solvent. Thus, returning the paraffin into its hardened and solid state.

Method of IHC or ICC Staining

In some embodiments, the instant specification is directed to a method for immunohistochemical (IHC) or immunocytochemistry (ICC) staining. In some embodiments, the instant specification is directed to a method for immunohistochemical (IHC) or immunocytochemistry (ICC) staining using the process record slide as described above.

In some embodiments, the IHC or ICC staining process includes: embedding a fixed sample into paraffin, and removing the paraffin to expose the antigen sites within the cellular structure of sample.

In some embodiments, removing the paraffin comprises: warming the paraffin into a semi-liquid state at a temperature ranging from 65 to 75 degrees C. for 3-10 minutes, then liquefying the semi-liquid paraffin with an aliphatic solvent, such as xylene or xylol followed by a rehydration sequence of anhydrous ethanol, 95% ethanol, 70% ethanol, 50% ethanol, and a salt- based buffer solution.

In some embodiments, the IHC or ICC staining process further includes removing the formaldehyde fixing to expose the antigen sites in the sample. In some embodiments, removing the formaldehyde fixing including performing a heat induced epitope retrieval (HIER) process, or performing a many cycle warm water antigen retrieval process.

In some embodiments, the HIER process includes breaking the Schiff base bond between the formaldehyde and tissue by subjecting the sample to heat in the presence of water. In some embodiments, subjecting the sample to heat comprises subject the sample to a temperature ranging from 89° C. to 95° C. In some embodiments, the sample is exposed to a buffer reagent when being subjected to heat. In some embodiments, the buffer reagent has pH ranging from 6 to 10, such as from 6 to 9. The choice of the pH of the reagent depends on the type of the sample, such as tissue type.

In some embodiments, the water-based antigen retrieval process includes subjecting the sample to a temperature about 10° C. higher than the melting temperature of the embedding paraffin, which ranges from about 60° C. to about 65° C. In some embodiments, the water-based antigen retrieval process includes subjecting the sample to soap and successive washes to dissolve and remove the paraffin.

It should be noted that operator errors or processing defects in the paraffin removal and fixation recovery can block the subsequent staining process and result in a false negative result. Although such false negative result can be detected by reviewing the staining results of the control targets in the process recording slide, the operator errors or processing defects would nonetheless result in waste of samples, time and resources, and should be avoided.

At this point, the antigen sites are exposed and the stain reagents can be applied to produce a signal indicating the presence and amount of the targeted antigen.

In some embodiments, the IHC or ICC staining process further includes applying one or more primary antibodies. If more than one primary antibody is applied, the antibodies need to be from different animal species to avoid cross-reaction by the secondary antibody. For example, if two primary antibodies are used and the first one is a mouse antibody, then the second primary antibody needs to be a non-mouse antibody like a rabbit antibody. According to these embodiments, the one or more primary antibody will bind to the matching antigen sites in the sample, as well as to the primary control target such as the protein/peptide antigen or the surrogate antigen. In some embodiments, the primary antibody includes an antibody targeting ER, PR, Her2, or Ki67.

Figure 11:
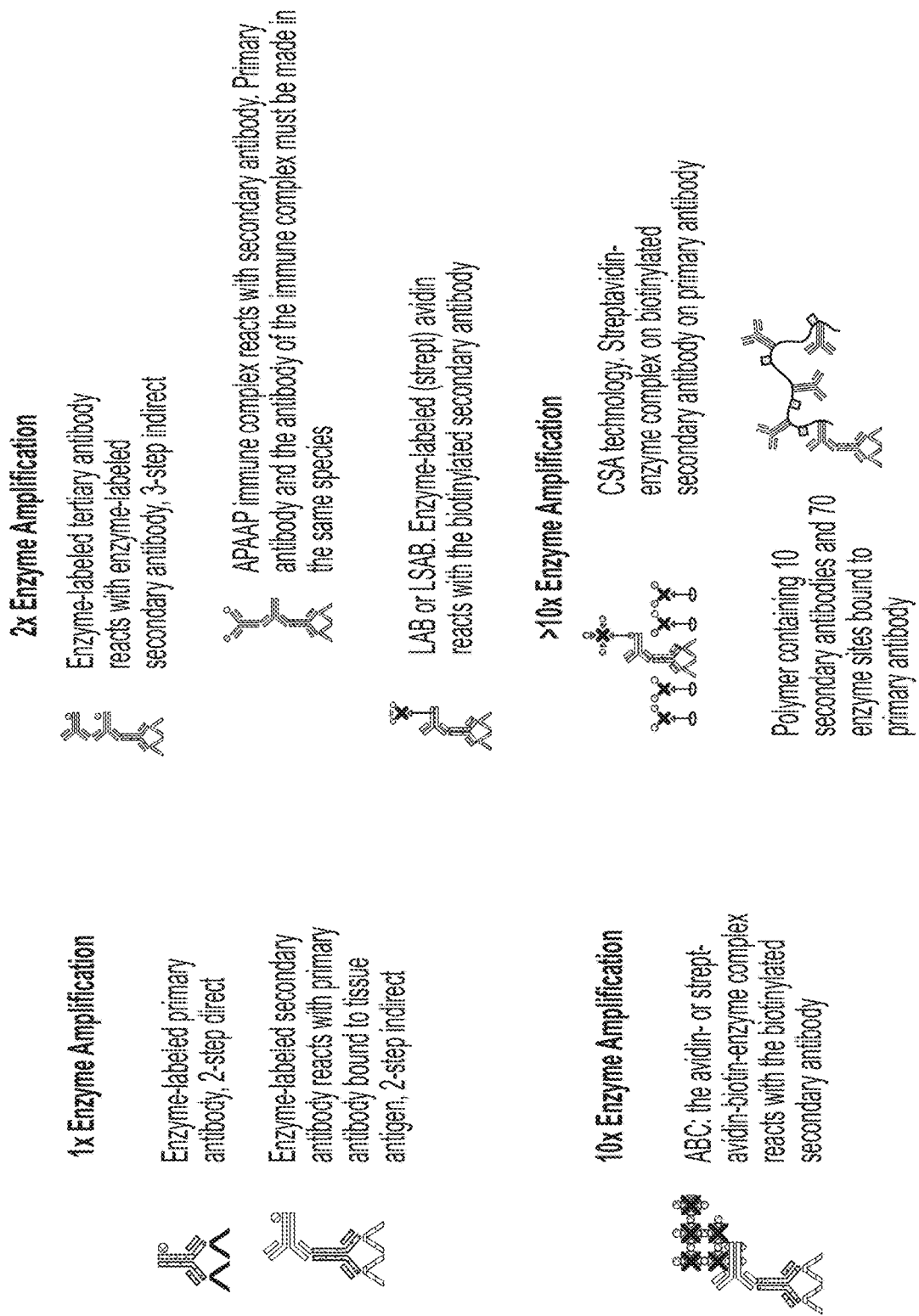
FIG. 11 is an enzyme amplification process in accordance with some embodiments.

Refer to FIG. 11, in some embodiments, the primary antibody is conjugated with a reporter, such as a chromogenic reporter, such as an enzyme chromogenic reporter. According to these embodiments, no secondary antibody is needed.

In some embodiments, the primary antibody is not conjugated with a reporter. According to these embodiments, a secondary antibody targeting the primary antibody is applied. In some embodiments, the secondary antibody is conjugated with the reporter.

Refers to FIG. 11, in some embodiments, to further amplify the signal of the antigen, a multistep signal amplification process is carried out. Examples of multistep signal amplification process includes: 2× gain for enzyme-labeled tertiary antibody reacts with enzyme-labeled secondary antibody, 3-step indirect; 2× gain for APAAP immune complex reacts with secondary antibody. In some embodiments, the primary antibody and the antibodies of the immune complex are made in the same species. The signal amplification process includes: LAB or LSAB, Enzyme-labeled (strept) avidin reacts with the biotinylated secondary antibody; >10× gain for CSA technology, Streptavidin-enzyme complex on biotintylated secondary antibody on primary antibody; >10× gain for a polymer containing 10 secondary antibodies and 70 enzyme sites bound to a single primary antibody.

In some embodiments, the reporter is an enzyme capable of causing a chromogen precipitation when a substrate is present. All arrive at the same end state of a chromogen precipitation.

In some embodiments, the reporter enzyme includes horseradish peroxidase (HRP), alkaline phosphatase (AP) or glucose oxidase.

In some embodiments, one or two of, three commonly used secondary stain groups and one of several counterstains are used: Horseradish peroxidase (HRP), alkaline phosphatase (AP), glucose oxidase and nuclear counterstains.

In some embodiments, the chromogen includes 3,3'-Diaminobenzidine (DAB), Amino-9-ethyl carbazole (AEC), DAB+Nickel enhancer, Fast Red, TMB, StayYellow, BCIP/NBT, BCIP/TNBT, Naphitol AS-MX phosphate+Fast Blue BB, Naphihol AS-MX phosphate+Fast Red TR, Naphitol AS-MX phosphate+new fuchsin, StayGreen, NBT, or combinations thereof.

In some embodiments, the substrate and reporter enzyme combination, as well as the result color is the follows:

| HRP (Horseraddish peroxidase) | | |
|---|---|---|
| DAB (3,3'-Diaminobenzidine) | >> | Brown to Red Brown |
| AEC (3-Amino-9-ethylcarbazole) | >> | Red |
| DAB + Nickel enhancer | >> | Black |
| TNB (3,3',5,5'-Tetramethylbenzidin) | >> | Blue |
| StayYellow | >> | Yellow |
| AP (Alkaline Phosphatase) | | |
| BCIP/NBT (5-bromo-4-chloro-3-indolyl-phosphate)/ (nitro blue tetrazolium) | >> | Blue |
| Naphthol AS-MX phosphate + Fast Blue | >> | Blue |
| Naphthol AS-MX phosphate + Fast Red | >> | Red |
| Naphthol AS-MX phosphate + new fuchsin | >> | Red |
| StayGreen | >> | Green |
| GO (Glucose oxidase) | | |
| Nitro blue tetrazolium chloride (NBT) | >> | Blue to purple |

In some embodiments, the IHC or ICC staining process further includes a counterstaining, such as a nuclear counterstaining. In some embodiments, the nuclear counterstaining uses one or more nuclear stains, such as hematoxylin that generates a blue color.

The choice of the staining substrate or compound can be made based on the color requirement, stability requirement, and regional regulatory standards.

For example, DAB is commonly used in countries such as the USA and China while AEC is commonly used in other countries. DAB is often used over AEC due to the fact that the brown-red color generated by DAB has higher saturation as compared to the red color of the AEC. However, AEC staining is more stable than DAB staining. Experiments show that the original DAB ages significantly over a short period of time, such that the color saturation drops noticeably within a 4-hour span. Newer versions of DAB incorporate stabilizers that extend the stability of the DAB from hours to days. DAB also has the propensity to be washed out during subsequent buffer wash cycles. AEC, on the other hand, remains stable for weeks to months.

Regulatory standards throughout the world seek, or insist, that validated controls be used to check reagents, methods, and instrumentation for processing of tissue sections and loose cells once such a technology becomes viable and available. Such regulatory controls have long been in place for hematology and clinical chemistry to validate the results and for quality assurance. The result of the controls testing is plotted in the form of a Levey-Jennings chart (Westgard et al. 1981). Westgard J, Barry P, Hunt M, Groth T (1981) "A multi-rule Shewhart chart for quality control in clinical chemistry". Clin Chem27:493-501.

Antigen Imaging Scale Extrapolation

In some embodiments, the method of IHC or ICC staining further includes estimating an antigen concentration in the co-resident patient sample by extrapolating the stained result of the primary and secondary targets.

In some embodiments, the method of IHC or ICC staining further includes determining the Process QC of the IHC or ICC staining steps by extrapolating the stained result of the primary and secondary targets.

Because the amount of the control targets deposited on the slide is predetermined, knowing the molecular mass, the number of control target molecules of each protein type in the deposit, the target's area, and the slide coating's porosity an active surface protein density of the target can be calculated.

The applied concentration, dispensed volume, and surface area on slide exposed to the reagent of primary antibody are known. It can be reasonably assumed that during the exposure time of the reagent that most of the suspended antibodies will have fallen down and been captured by receptive antigen sites. Only those that fall directly over antigen sites will become captured and the balance will be washed away by a buffer wash step. Thus, the deposited antibody concentration can be established under proper conditions, for example, when the concentration is greater than 25% above cutoff and less than 25% from saturation. As used herein, the term "cutoff" is defined as insufficient target site density to capture the applied the protein concentration; saturation is defined as a concentration at which not all of the applied protein could be captured.

Knowing the primary dilution ratio, the correct primary target density target can be chosen and the primary concentration can be validated.

In one embodiment of the present invention, each secondary and primary target is a mix blend of [(mouse or rabbit IgG)+(donkey IgG+crosslinker+fungal inhibitor)] or [(KLH with antigen A or KLH with antigen B)+(unconjugated KLH+crosslinker+fungal inhibitor)] or surrogate antigen [(Donkey-anti-Mouse IgG or Donkey-anti-Rabbit IgG)+crosslinker+donkey IgG+fungal inhibitor]. Each dot has the same volume of total proteins, but the mix ratio is adjusted slightly so that the atomic masses are different between the proteins composing a specific target;

The molecular weight of some exemplary proteins are listed below:

Mouse IgG=155 kDa
Rabbit IgG=150 kDa
Donkey IgG, Donkey-anti-Mouse, and Donkey-anti-Rabbit=160 kDa
Protein A=42 kDa
Protein G=58 or 65 kDa
Protein A/G=50 kDa
Protein L=76 kDa
Chicken IgY=180 kDa
KLH subunits: KLH1 and KLH2=350 and 390 kDa, respectively.

In another embodiment of the present invention, the 2D secondary target gradient includes stepped dilution increments of 1 to 1000:1. In some embodiments, the dilution follows a −20log(dilution) profile, wherein the dilution increments in −3 dBd steps. The terms −20log(dilution) =dBd, both describe the dilutions on a semi-logarithmic basis in order to linearize the data so that modifying terms can be easily applied. The term (dillution) refers to the dilution X where Xis [1 . . . 1000] equating to 1:1 to 1,000:1. The term dBd is defined as decibels of dilution or dilution strength. The modifying terms include antigen retrieval damage, enzyme gain, or primary antibody reagent dilution;

The secondary stain incorporates an enzyme gain function between 1 and 20×, which is a function of the construction of the stain reagent. Therefore, as the gain rises the lower concentration secondary target will shift into saturation whereas when the gain drops to one only the high concentration secondary targets will be visibly stained;

Because of the considerable size difference between the secondary and conjugated primary target proteins based on KLH subunits with peptides, the dummy diluent must be un-activated KLH units as the peptides do make for a noticeable change in mass to the KLH subunit.

The expected binding capacity of the KLH subunit to Protein A, G, and A/G is predicted to be between four and six proteins. For a suitable dummy the KLH needs to be joined with Chicken IgY, which is completely non-reactive to any of the Protein A, G, A/G, or L proteins. While the chicken IgY is nearly 4× bigger than Protein A/G then will be less bound to the KLH so the end result is about the same. Either choice puts the mass to 650 to 700 kDa. As detailed below for mouse and rabbit IgG the KLH subunit mass figure can be plugged in and the calculations performed.

In another embodiment of the present invention, the primary targets can be fabricated from Protein A, G, or A/G. The primary antibody is dominantly based on either a mouse IgG or rabbit IgG host Fc domains. However, the FcyRI sites are found on mouse IgG1 and rabbit IgG. Protein A binds strongly to rabbit IgG, but weakly to mouse IgG1. Protein G binds strongly to rabbit IgG and medium to mouse IgG1. Protein A/G binds strongly to rabbit IgG and medium to mouse IgG1. Protein L binds strongly to mouse IgG1 and weakly to rabbit IgG in the Fab light chain versus the FcyRI of the others. In some embodiments, Protein G or A/G are used. Both appear as dipole structures, wherein they support only a single connection to a primary antibody.

Protein A, G, A/G and L bind to most placenta mammals IgG, which means that the blocking step before the application of the secondary stain kit will not work if BSA (bovine serum albumin) is used as BSA will not bind to these proteins. In particular, goat is blocked from binding to Proteins A, G, A/G or L. This is different from other approaches, as most secondary stain kits use goat as a host protein at some step. Thus, it is strongly recommended that a blocker be based on the equine family: horse, donkey, taper, and rhino IgG proteins. The equine family split away genetically early from the placenta mammals, enough so that it is largely non-reactive to the secondary stain reagents, but will bind to Protein A, G, and A/G. sufficiently to block the unreacted primary target sites.

Because the binding connection to the primary antibody always leaves one of the two FcyRI sites open for reacting with the secondary antibody, the captured primary antibody must be functionally intact with at least one FcyRI site available to support the secondary staining. Thus, the captured primary antibody that becomes stained represents the actual applied concentration versus the primary's assay/dilution figure.

With an average primary antibody atomic mass is 150 kDa, the molecular weight of a single antibody molecule is 150 kDa ($1.6605 \times 10^{12}$), which equals a weight of $249 \times 10^{-12}$ ng. Assuming a single area of the slide is the only part exposed, then the amount of applied primary reagent can be determined. For example, when a closed capillary gap having an inside dimensions of 20.3 mmsq×0.14 mm is used, the volume is 57.2 µL. Ratio for a target area of 1 micron, which yields 2.832 nl of the applied primary antibody reagent;

The primary antibody reagent is diluted from a concentrate to an intermediate dilution of 10 ug/ml. The intermediate dilution is then diluted, from 1:1 to 1000:1, for application onto the slide. This results in a deposition of 31.5 to 7.08 antibodies onto a 1 micron area for a dilution of 1:1 to 25.1:1 respectively.

To ensure 100% capture ability the primary target should have a safety factor ranging from 100 to 1000×. When the 1000× option is chosen the primary target needs to contain $4 \times 10^6$ antigen sites. While the KHL subunits are bigger than the applied antibodies, the increase is not enough to change the number of captured antibodies beyond 1:1. Each KLH subunit has an average atomic mass of 370 kDa which equates to a weight of $614.4 \times 10^{-12}$ ng.

The volume of a protein molecule can be approximated from the molecular weight of the protein and an average protein partial specific volume (partial specific volume=volume/molecular weight). The average of experimentally determined partial specific volumes for soluble, globular proteins is ~0.73 cm$^3$/g. This value varies from protein to protein, but the range is narrow. The equation reduces down to a protein volume of ~$(1.212 \times 10^3 \times MW)$ nm$^3$. Thus, for the KLH subunit the individual volume is 448.44 nm$^3$. Assuming that the protein is a sphere, the diameter of the sphere is calculated as $0.132 \times MW^{1/3}$ in nm. According to this calculation method, the diameter of a KLH subunit is about 9.436 nm;

For a control target dot having a diameter of 1 mm and includes a monolayer of the KLH subunits, $11.237 \times 10^{27}$ proteins are needed. For the active target density of $4 \times 10^6$ proteins the minimum dilution ratio is $1:2.8 \times 10^{21}$. In practical terms, any dilution approaching 1:1000 is workable as the evaluation of the primary antibody is dominated by its active protein concentration. Thus, the target density is only limited by its low concentration floor value.

In one embodiment, the secondary target arrays are stepped dilution increments of 1 to 1000:1. A linear slope for the dilution occurs as dBd=−20log(dilution). For the dilution range of 1 to 1,000:1, the semi-log range is 0 dB to −60 dBd. In some embodiments, −3 dB stepping dilution of the secondary target results in a dilution series of −0, −3, −6, −9, −12, −15, −18, −21 dBd.

The secondary and primary target arrays are both semi-reversibly fixed and therefore undergo a smaller degree of degradation comparing to the sample or the AR targets during the AR process. The degradation comes from protein segments that break free rather than complete proteins. In some embodiments, as the AR process continues to act on the protein targets and the sample section the AR damage considered as the gradient scale pattern shifts towards the 100% position. On the other hand, the secondary enzyme gain causes the gradient array to shift towards the 10% position. In some embodiments, the enzyme gains are 1, 2, 4, 5, 8, 10, 15, or 20. This translates into shifting the secondary array towards the 10% target by:

| 1. | 20x | all targets shift −26 dBd |
|---|---|---|
| 2. | 15x | all targets shift −23.52 |
| 3. | 10x | all targets shift −20 |
| 4. | 5x | all targets shift −13.98 |
| 5. | 4x | all targets shift −12.04 |
| 6. | 2x | all targets shift −6.02 |
| 7. | 1x | only 2D 100% dot near black |

Typically, AR damage that shifts the secondary array towards the 100% position by three or more dots is considered to be excessive and the staining should be redone using a higher enzyme gain secondary stain kit or a higher concentration of antibody.

The primary antigen target color density is thus the collective sum of the antibody concentration times the enzyme gain of the secondary stain kit. While the secondary target density is only that of the enzyme gain times the secondary target protein concentration;

Depending on the digital imaging system, changes in the illumination intensity will shift the dynamic range of the image into saturation (getting darker) or cutoff (getting lighter). These changes shift the antigen color scale while the antigen density numeric scale will not. Thus, the numeric scale is independent and the color scale dependent on the illumination intensity.

Figure 13:
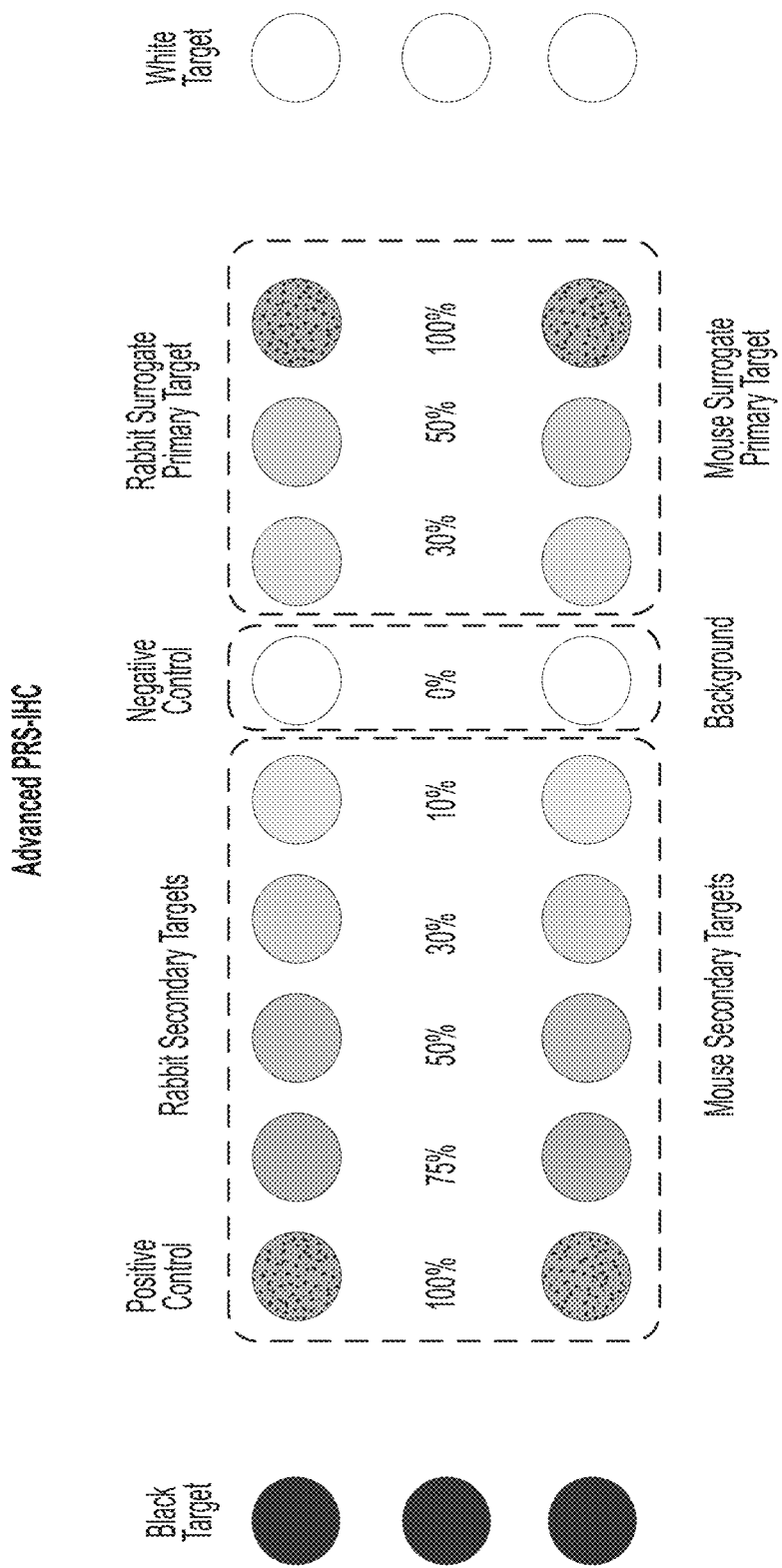
FIG. 13 is a dual primary antibody control slide that supports the use of one mouse based primary antibody and one rabbit based primary antibody in accordance with some embodiments.

In one embodiment of the present invention, see FIG. 13, within the control area 140, the aforementioned secondary protein target arrays are formed as two lines: one of mouse IgG and the other rabbit IgG mixed with a dummy IgG blood serum protein to form a five or more member gradient density series that progresses from a maximum density to a minimum density in a −20log(dilution) linear slope, wherein the dilutions may range between 1:1 to 1,000:1 after the initial 1000:1 dilution.

In another embodiment of the present invention, the aforementioned secondary target arrays are formed as three concentrations of 33, 16.5, and 4% of the mouse IgG or the rabbit IgG mixed with donkey IgG.

In another embodiment, in the last process step, those antigen sites identified become colored by chromogen precipitation. Thus, the mouse and rabbit target array reflects the −20log(dilution) linear slope of secondary stain kit chromogen precipitation or the target arrays reflect the secondary stain reactivity and enzyme gain.

In another embodiment, the solution for the method for forming the primary target density gradient array is predicated on successfully composing the target mixtures, depositing them onto the adhesive coated slide, and having a covalent bond between the adhesive and the target materials.

In another embodiment, deducing that the target arrays are successfully deposited and the both the primary and secondary stain reagents perform reasonably, a curve fitting between the data sets can be done by computer algorithm. In another embodiment, the primary stain is selected from any IHC or ICC approved antibody that including a mouse or rabbit host protein that is not also conjugated to a fluorescent marker or integrated with an enzyme site (such as HRP or AP). In another embodiment, the secondary stain is include secondary stains having enzyme gains of 1× through 25×, that are each uniquely independent between mouse and rabbit, which each use a different color chromogen.

In another embodiment of the present invention, it is pertinent to note that the performance result in an absolute basis on one slide may not be identical to another slide done at another time. This comes from the fact that the secondary stain kits vary in performance lot to lot as does the primary conjugated primary antibody. However, the results of the process record slides can be validated by the control targets and provide equivalence to another slide done using different stain reagents.

In some embodiments, the primary antigen concentration scale is then applied to the co-resident tissue section to access the tissue section for detecting cellular defects, such as cancer.

Various embodiments are described herein as examples. It will be apparent to those skilled in the art that various modifications may be made and other embodiments can be used without departing from the broader scope of the invention(s) presented herein. These and other variations upon the exemplary embodiments are intended to be covered by the present invention(s).

EXAMPLES

The following examples are presented in a way to the illustration of the invention and should not be construed to limit the scope of the invention in any manner.

Example 1 Paraffin Shield Coating with Spray Application Method

The surface of the slide is sprayed over with low airflow. In some embodiments, a low liquid to air mix is used. The mixture is sprayed onto the slide, through a mask, to cover the control targets. Typically, 1-2 passes are performed to form a layer having a thickness of less than 5 microns without the need to reheat to flow the paraffin seal. The paraffin mixture reservoir and spray head are both heated to slightly higher than 56° C. to ensure the paraffin is sprayed as a fluid and remains as a fluid while in flight to the slide. Spray coverage from the head is nominally 0.375" in width. The deposited paraffin mixture is reflowed by raising the ambient heat to 60° C. for one minute, which drives out the solvent and enables the paraffin to return to a hardened state when cooled.

Example 2 Paraffin Shield Coating with Screen Printing Method

A stainless steel printing screen is heated by passing an electrical current through the wires of the screen from two parallel sides. The temperature of the screen is slightly below the melting temperature of paraffin so that paraffin paste does not weep through to the bottom side of the screen. At such temperatures, the paraffin behaves closer to a paste than a liquid. The deposited paraffin is reflowed by raising the ambient heat to 60° C. for one minute. Any solvent in the applied paraffin mixture is then driven out and the paraffin returns to hardened state.

Example 3 Paraffin Shield Coating with Ink Jet Method

An inkjet head incorporating an integrated heater is to be used to keep the paraffin in the liquid state. An aliphatic solvent, Zylol for example, is used to change the paraffin from a solid to a liquid. The deposited paraffin mixture is reflowed by raising the ambient heat to 60° C. for one minute. The solvent in the applied paraffin mixture is then driven out and the paraffin returns to hardened state.

Example 4 Paraffin Shield Coating with Roller Transfer Printing Method

A heated roller pulls up a film of paraffin from a heated reservoir. The roller then transfers the film of paraffin onto the slide much in the same fashion as a painting a wall with a napped roller. The deposited paraffin is reflowed by raising the ambient heat to 60° C. for one minute. The solvent in the applied paraffin mixture is then driven out and the paraffin returns to hardened state.

Example 5 Antigen Retrieval Exposure Time Versus Degradation to a Simple Logarithm Series of PRS Secondary Targets The test study sought to verify that the changes in AR exposure time would be seen in 2D secondary targets and the AR targets.

The expected result was a linear slope of antigen retrieval exposure time and signal strength reduction. Indeed, when the time taken for the AR buffer to reach above 89° C. is taken out of consideration, the plotted slope was linear. Using an 8-bit digitization with the PRS black/white targets to set the white balance and contrast optimally, a slope of 1.3 lsb/minute, +/−0.2 lsb was obtained. The experiment shows that the signals of the AR targets and the secondary targets reduces in a linear manner upon AR exposure for 20 minutes past the 89° C. time mark. After the 20 minutes mark, due to that 50% or more of the control target was under serious stress, the usefulness of the secondary targets was compromised.

Example 6 Consistency of the Secondary Targets

The test study had two factors being explored:
I. Dot-to-dot comparison among a batch of slides assembled using a single lot code secondary protein source and dilutions.
II. Dot-to-dot comparison among slides assembled using different lot code secondary protein and dilutions.

Tests were performed using 100% and 40% target formulations. One hundred slides were printed and all processed with an avidin-biotin complex (ABC) type mouse and rabbit secondary stain kit from Scytek. Antigen retrieval was not performed as it adds an additional variable. The distribution of both was within 1.5%.

Example 7 Selection of Dummy Protein

Ten different secondary arrays were constructed using two different lots of mouse, rabbit, and bovine IgG proteins. The arrays were constructed with a dilution of 100, 40, and 20% of the IgG proteins. The distribution was within 1.5% for the 100 and 40% dilution groups. The 20% dilution groups showed an unexpected increase in stain strength. The instant inventors discovered that the issue was due to an unexpected interaction between the bovine IgG and biotinylated goat-anti-polyvalent reagent from the ABC stain kit. The problem was solved by replacing the bovine IgG with donkey proteins. The test was repeated and the 20% group is now within 1.5%.

Example 8 Quality Control using Secondary Logarithm Series PRS

Figure 6:
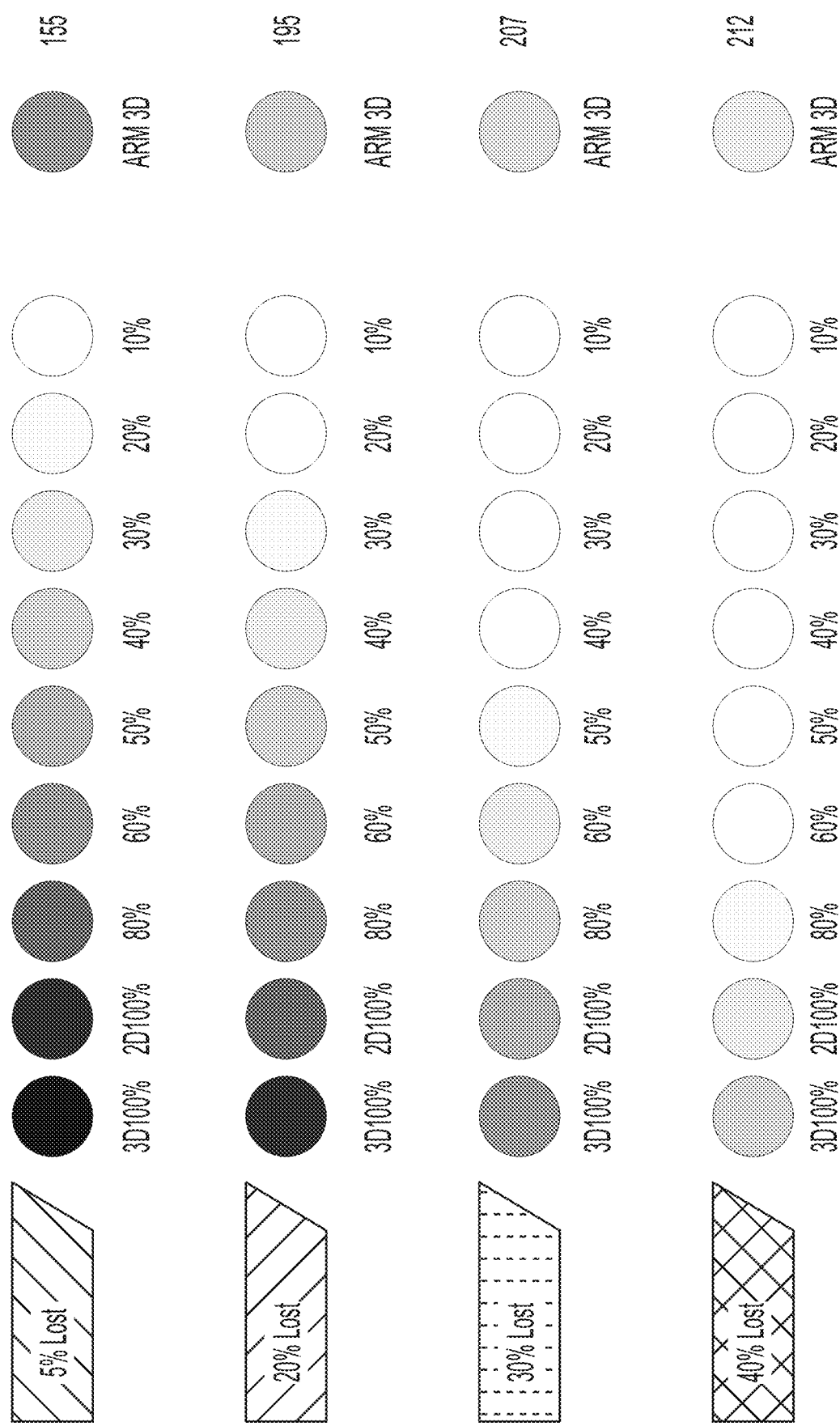
FIG. 6 is an antigen retrieval target of the slide in accordance with some embodiments.
Figure 7:
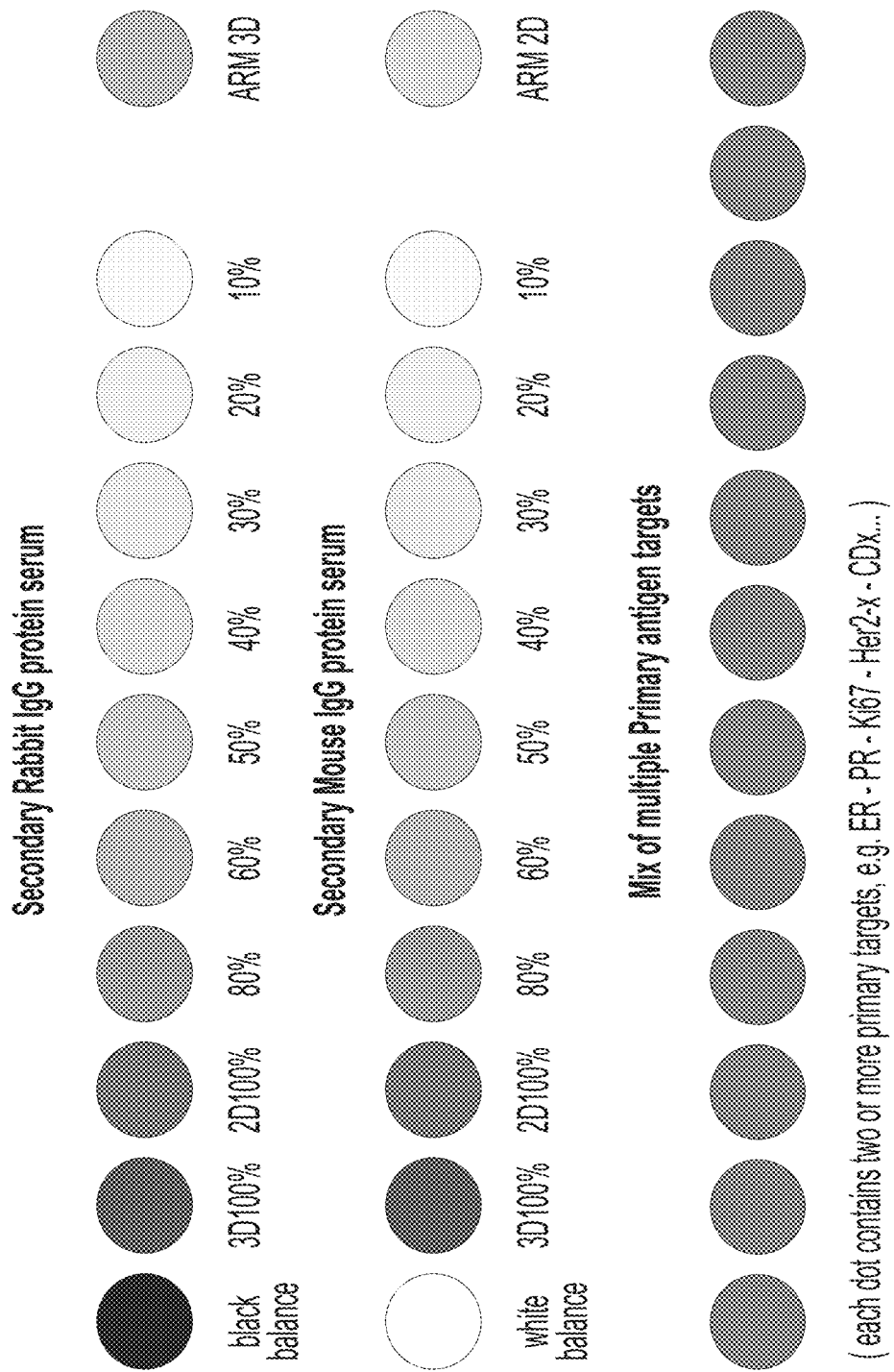
FIG. 7 is a control area of the slide in accordance with some embodiments.
Figure 8B:
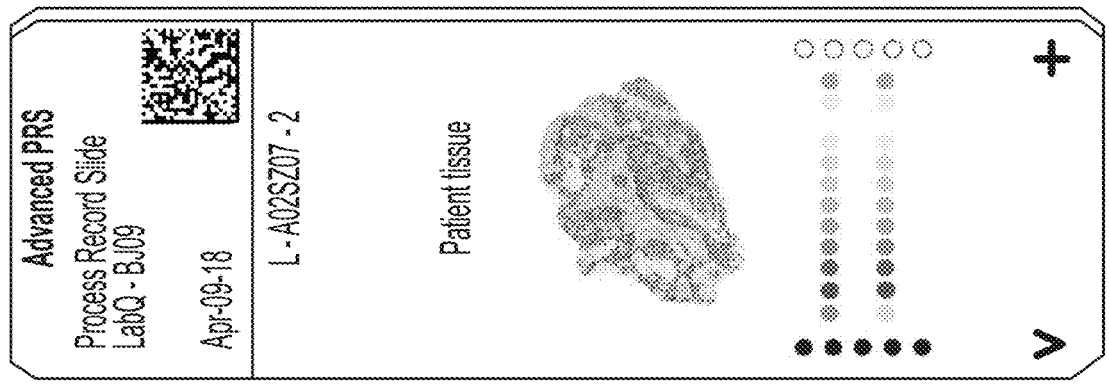
FIGS. 8A and 8B are slides after the staining process in accordance with some embodiments.
Figure 8A:
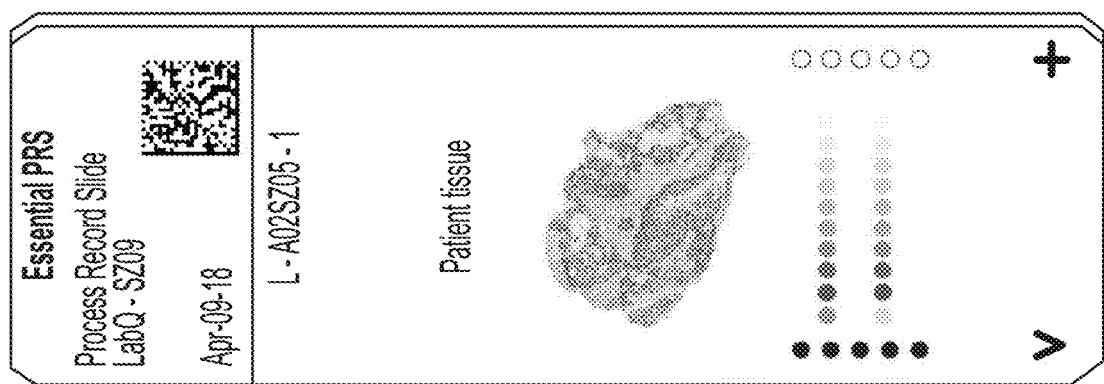

In QC mode, the co-resident targets provide IHC process feedback as is illustrated in FIG. 6.

Referring to FIG. 6, there four arrays of (50:50 mix of mouse & rabbit) secondary targets exposed to the degree of antigen retrieval performed from within nominal, mildly over, over, and excessively over (5, 10, 30, and 40% respectively). The staining results come from four different slides representing each of the listed conditions above. The antigen retrieval process seeks to unmask the antigen sites by reversing the Schiff base bond between the formaldehyde and proteins. The speed at which the antigens become exposed depends upon the temperature of the reaction. As the temperature is increased, the opportunity occurs for nucleated boiling. The nucleated boiling causes physical damage to both the tissue and protein deposits. Ideally, the antigen retrieval (AR) activity is uniform through the slide, however, in practice this is often not the case and areas having slightly more or less antigen retrieval activity exists. If such un-uniformity of antigen retrieval activity is ignored, the following can be used to indicate that the slide will be usable for diagnostic determination.

If the AR is insufficient or excessive, the secondary array may not be able to reflect the failure. The two AR targets however, will signal the insufficient or excessive failure conditions.

a. Low AR is seen as the 2D/3D under fixed and 2D over fixed targets are both black. The secondary arrays will appear as perfect with no AR shifting left of the targets. Low AR activity can occur from the following situations in the IHC stainer:
  i. AR Heater not working or set well below 80° C.
  ii. AR buffer has a neutral pH 7, rather than 6 or 9
  iii. Exposure time too short
b. High AR is seen as the 2D/3D under fixed is very bleached and the 2D over fixed target is less than 50% black. The secondary arrays will be largely bleached out as well. High AR activity can occur from the following situations in the IHC stainer:
  i. Heater operating at temperature >95° C.
  ii. Exposure time too long
c. Chromogen precipitation error can arise under two situations:
  i. If at the high concentration secondary targets the stain intensity dips rather than is at maximum darkness. The secondary array should be always increasing vs. site density. If not then the chromogen precipitation has exhausted the secondary reagent kit capacity. The solution is to increase the primary antibody dilution (same as reducing the antibody concentration).
  ii. The chromogen reagent has deteriorated since being activated (often occurs with DAB). The solution is to use a new DAB mixture.

The staining can experience saturation or cutoff as a function of the concentration of the primary antibody and the enzyme gain of the secondary stain kit. Saturation is when the density of the enzyme sites exceeds the capacity to precipitate colorant from the chromogen. In other words, the stain color is as dark as can be realized. Cutoff occurs when the concentration of the primary antibody and enzyme gain of the secondary stain kit are too low, resulting in insufficient colorant precipitation to be seen. The two factors cause the darkness of the secondary line to shift to saturation (100%) or cutoff (0%). Based on FIG. 6, this movement is seen as the number of targets that are visible. As the secondary enzyme gain increases the 100% dot density shifts towards the 0% position. The common enzyme gains are: 1, 2, 4, 5, 8, 10, 15, and 20. These translate into shifting the secondary array towards the 0% position by:

20× all targets shift −26 dBd
15× all targets shift −23.52
10× all targets shift −20
5× all targets shift −13.98
4× all targets shift −12.04
2× all targets shift −6.02
1× only 2D 100% dot near black If the primary target array is present an increase in secondary enzyme gain shifts the stain density towards the low primary concentration dot. The same is true if the primary antibody concentration is increased. The antigen retrieval process will cause both primary and secondary targets to be degraded to some level, which reverses the shift towards cutoff. If at the end of the IHC staining there are three or more dots that have disappeared the slide would be considered to have had excessive antigen retrieval duration, temperature, or both and too much antigen presence has been lost on the tissue making diagnostic interpretation marginal. This decision is independent of the efficacy of the primary antibody as the secondary staining is already been shown to be compromised. Nothing on the antibody step can overcome this damage level.

Example 9 PRS Tracks Illumination Level with Antigen Density Scale

Figure 10:
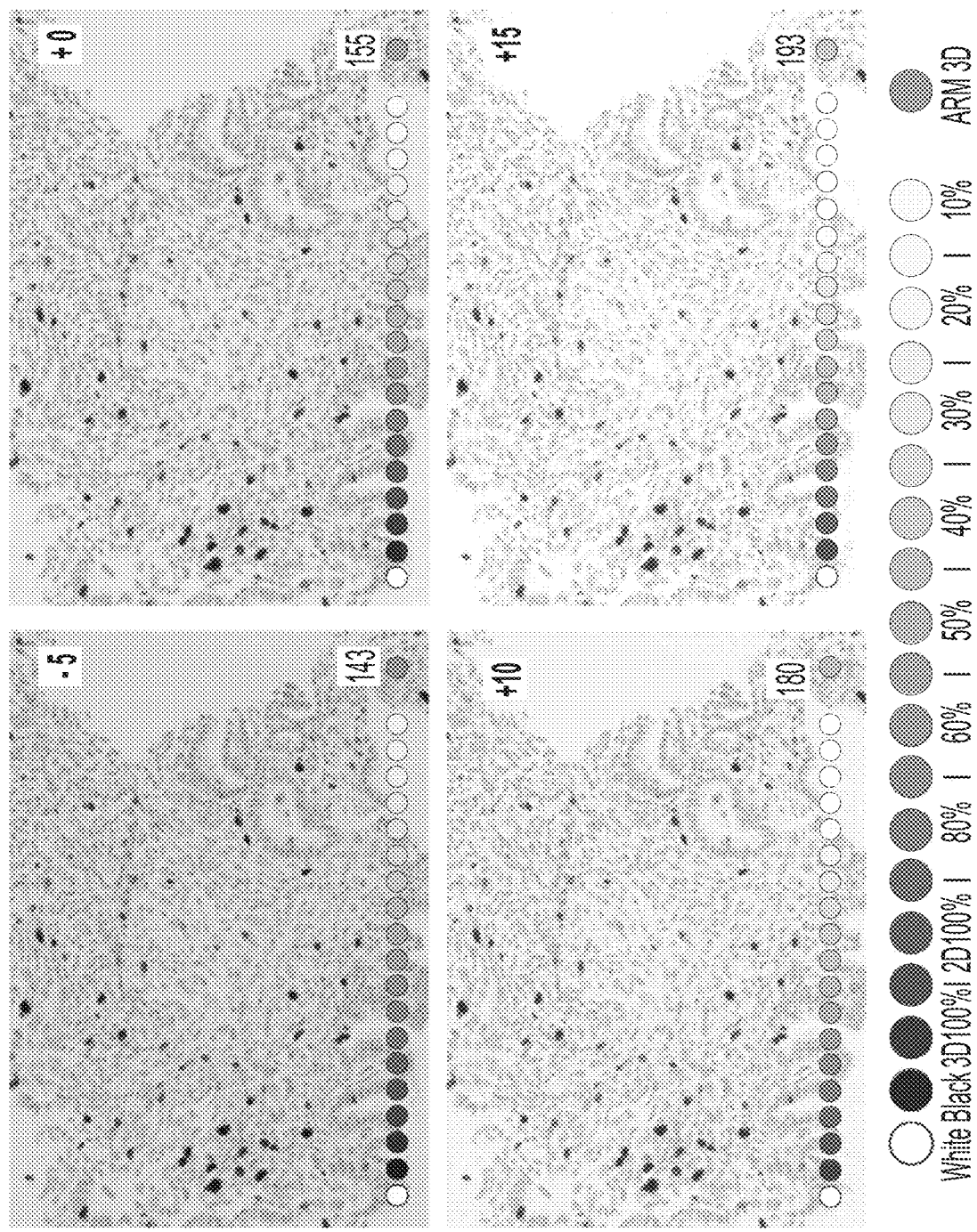
FIG. 10 is an imaging result of a stained slide in accordance with some embodiments.

Viewing a microscope slide through a conventional microscope is subjective in regards to the transmitted light illumination level. In whole slide imaging (WSI), the scanner uses a perfect white and black hole to establish the white balance and contrast. Such is not the case with manual microscopes. FIG. 10 illustrates the effect to the image as the illumination level is too dark (−5% from optimal), optimal (+0), and too bright as in (+10 or +15%). When the light level is below optimal there is compression of stain density. In terms of cancer stages this could shift the diagnosis one stage higher than it should be. When the light level is above optimal there is bleaching of the image. In terms of cancer stages this could shift the diagnosis one stage lower than it should be. The antigen color density and numeric ruler is developed from the primary and secondary targets and can be superimposed upon the WSI image. The numerical scale is the independent term while the color density is the dependent term. When the antigen density color and numeric ruler is applied to the WSI the numeric scale remains fixed as the user shifts the illumination level up or down. The color density scale on the other hand shifts as the illumination level changes. The advantage is that the user has the choice to shift the apparent illumination up/down to best 'see' features on the tissue image while never losing the numeric relationship to color density. This will also be functional as the magnification is changed.

Example 10 Construction of Antigen Density Ruler

According to some embodiments, two types of antigen density ruler are developed.
1. Type A uses a secondary target array, which is based on the assumption that the primary antibody is always applied with less than 10% excess antibody vs. tissue antigen sites.
2. Type B uses a primary target array (a primary antigen gradient density array).

Type A: Secondary Only Based Antigen Ruler

This form uses only the secondary target array. The passed in information that is imbedded in the 2D bar code includes the (a) primary antibody data: host species for the antibody and dilution in −dBd (dBd is dB dilution) and (b) secondary enzyme gain.

The secondary gradient density target array is composed of known concentrations of secondary target proteins following an −3 dBd decrement between targets. The maximum concentration is chosen by the least dilution that is used for the primary antibody. Users often take the concentration specification provided by the antibody reagent manufacturer and dilute to a constant intermediate concentration of 1 ug/ml. From that all other dilutions are made as needed to accommodate the different tissue types. In general, the second set of primary antibody dilutions range between 1:1 and 1,000:1.

To accommodate the range of secondary enzyme gain the secondary array includes of a wider range of dilutions. Thus, with −3 dBd steps the lowest dilution of the secondary array starts at 1,000:1 or −60 dBd, which is represented by SdBd (secondary dB dilution). The maximum of the 8-dot series then becomes −0 dBd or 1:1. The action of the antigen retrieval degrades the secondary targets which is represented by ARdBd (antigen retrieval dB dilution). Each dot, one of eight, in the secondary array represents an −3 dBd increment. The antigen retrieval loss for the loss of two targets (no longer visible) would be +6 dBd. This means the secondary array is (−S+AR)dBd for the 2D targets or [+6 to −54 dBd]. The antibody concentration and the secondary enzyme gain is now factored in. The antibody concentration would be AdBd, while the enzyme gain is EdBd. Thus, the secondary array would be (−S+AR−E)dBd, while the tissue would be (+AR−E+A)dBd. The next factor that applied is the 100% 2D to 3D differential. The stain difference between the 3D objects in the 100% 2D/3D target and the 100% 2D represents the secondary stain chromogen precipitation constant, which is used to assign the color density to the numerical scale and is assigned to DdBd. The difference in color density is applied to each of the 2D targets in the array. Thus, the 2D array presents in stain color density as (+AR−E+A+D)dBd.

If the enzyme gain was 10× then E=−20 dBd. The 2D secondary array would then become: −14, −17, −20, −23, −26, −29, blank, blank dBd. The two dots towards 0% having been damaged enough by the antigen retrieval process that they are unrecoverable by the staining and thus, blank. If for example the 2D/3D color density difference is 10× then D=+20 dBd bringing the 3D secondary array to −34, −37, −40, −43, −46, −49, blank, blank dBd. It is assumed that the primary antibody reagents will find suitable antigen sites in the primary targets that 100% yield takes place. It is also assumed that while there are many more than two antigen peptide strands per KLH protein that only one antibody can effectively bind and become stained per KLH protein. Any additional antibodies finding a suitable antigen on the same KLH protein will be prevented from completion by the secondary stain because of overlapping occupancy. Therefore, the number of antigen sites per primary antigen carried protein that can become detected is one. Since the primary targets contain the same number of proteins per micron as the secondary the primary dilution from the 500ug/ml antibody master is then applied to the secondary array data to adjust the secondary color density to numeric antigen density. Monitoring the secondary targets, choose the target that has a middle color density. The middle color density being defined as the 50% point between maximum black and maximum white. The point then equates to 1.5 dBd out of the 3 dBd range. That point then functions as the anchor upon which the antigen density ruler is established. Using the last target range above the midpoint becomes −41.5 dBd.

The secondary targets are diluted to a 10 μg/mL master dilution. Each array is a blend of mouse or rabbit mixed with donkey IgG proteins. While the proteins all have different atomic mass's the following will assume all are 150 kDa and that the total number of proteins per target dot is constant the mix ratio is not. For now, only the reactive protein concentration is being considered. At 150 kDa the individual protein molecular weight MW=249.07×10$^{-12}$ ng. The standard target dot is 1 mm in diameter. If the printed deposit is 1 μm thick, and the deposit concentration is 10 μg/mL, 31.5×10$^6$ proteins will be deposited. A 1 μm diameter area would then have 31.5 proteins. If we allow that one protein equates to 1 antigen site then the antigen density can be established. The secondary array uses the same number of proteins per deposit, but the ratio between mouse or rabbit and donkey changes as the concentration of the Mouse or Rabbit is reduced. The 100% target is entirely Mouse or Rabbit and is matched to the 0 dBd point on the ruler.

The secondary staining kit will only stain on the tissue when a primary antibody binds to an antigen site on the tissue. The concentration of the applied antibody is not particularly limited, except that a sufficient antibody concentration is provided to bind to the available antigen sites. Thus, the antigen density measurement on the tissue remains a constant, but the numeric values is corrected for antigen retrieval damage and secondary enzyme gain. The color density vs. numeric measurement is then harmonized.

In the previous example the enzyme gain is 10× and the antigen retrieval has caused the loss of two dots from the secondary array. The enzyme gain is −20 dBd while the antigen retrieval loss is +6 dBd. The result is −14 dBd. The dilutions then translate to:

| Numeric Density dBd | Color Density dBd | % Target Mouse/Rabbit: Donkey | Antigen Density Mouse/Rabbit in 1 μm$^2$ |
|---|---|---|---|
| 0 | −14 | 100 | 31.5 |
| −3 | −17 | 70.8 | 23.32 |
| −6 | −20 | 50.1 | 15.78 |
| −9 | −23 | 35.5 | 11.18 |
| −12 | −26 | 25.1 | 7.90 |
| −15 | −29 | 17.78 | 5.60 |
| −17 | −32 | 12.59 | 3.96 |
| −20 | −35 | 9.9 | 3.12 |

Type B: Primary Antigen Based Ruler

This form uses both the primary and secondary target arrays. The passed in information that is imbedded in the 2D bar code includes the (a) primary antibody data: host species for the antibody and dilution in dBd and (b) secondary enzyme gain. The lot code data includes the information about which primary target combination is in use.

If a primary target series is present it would be 3-dots wherein the most concentrated dot would be at the same 100% concentration as the secondary array, but the dots are spaced apart in −6 dBd steps. In effect, the primary array and secondary array have the same dilution slope. The primary targets become: −0, −6, −12 dBd and are represented as PdBd (primary dB dilution). It is reasonable to expect that the antigen retrieval will damage will nearly identical to that of the secondary array. The primary array is acted upon by the secondary stain and thus experiences the same enzyme gain function. Thus, the primary array would be (−A+AR−E)dBd, where the primary target density is controlled by the primary antibody dilution. The only requirement is that P is always greater than A. For 10× enzyme gain=−20 dBd and +6dbd antigen retrieval loss the primary array is −20, −26, −32 dBd. The antigen retrieval loss does not act upon the primary targets enough to blank them out, based on the impact to the secondary array. While the secondary array is sufficient to produce the antigen density rulers it is important to verify that the primary dilution was correctly applied. Thus, the primary targets function in that capacity.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A control target array comprising:
   a first plurality of control targets, wherein each of the first plurality of control targets has a similar chemical or biochemical property, and the control target array is configured to:
   indicate an error and performance measure of intermediate steps during an immunohistochemical or an immunochemical detection process, and
   provide a reference for qualitatively or quantitatively determining a color and antigen density of stained tissue or cells.

2. The control target array of claim 1, further comprising a second plurality of control targets, wherein each of the second plurality of control targets has a similar chemical or biochemical property different from the chemical or biochemical property of the first plurality of control targets.

3. The control target array of claim 2, wherein the second plurality of control targets comprises a secondary target loading dot, the secondary target loading dot comprises a plurality of secondary targets, and each of the plurality of secondary targets comprises:
   a host protein of a primary antibody used in the immunohistochemical or the immunochemical detection process; and
   a dummy protein.

4. The control target array of claim 3, wherein each of the second plurality of control targets comprises a same host protein, and each of the first plurality of control targets comprises different host proteins.

5. The control target array of claim 1, wherein the first plurality of control targets comprises:
   a plurality of target loading dots, wherein each primary target loading dot of the plurality target loading dots comprises a protein site including a protein reactive to a host FcyRI peptide on a primary antibody, the protein is reactive to a singular or plurality of primary antibody hosts, and each protein site immobilizes a single primary antibody protein.

6. The control target array of claim 5, wherein the FcyRI peptide is coupled to a carrier protein, and the carrier protein comprises a non-reactive protein, the non-reactive protein is non-reactive to a secondary stain reagent used in the immunohistochemical or the immunochemical detection process.

7. The control target array of claim 1, wherein the first plurality of control targets comprises a plurality of primary target loading dots, each primary target loading dot of the plurality of primary target loading dots comprises a same reactive FcyRI peptide, each primary target loading dot of the plurality of primary target loading dots has a different concentration of the reactive FcyRI peptide from each other primary target loading dot of the plurality of primary target loading dots.

8. The control target array of claim 1, wherein the first plurality of control targets comprises a plurality of primary target loading dots, each primary target loading dot of the plurality of primary target loading dots comprises a different reactive peptide, each primary target loading dot of the plurality of primary target loading dots has a different concentration of the reactive peptide from each other primary target loading dot of the plurality of primary target loading dots.

9. The control target array of claim 1, wherein the first plurality of control targets comprises a primary target loading dot, the primary target loading dot comprises a plurality of primary targets, and each of the plurality of primary target comprises an antibody against a host protein of the primary antibody used in the immunohistochemical or the immunochemical detection process.

10. The control target array of claim 1, wherein the first plurality of control targets comprises a primary loading dot, the primary target loading dot comprises a plurality of primary targets, and each of the plurality of primary target comprises Protein A, Protein G, Protein A/G, or Protein L against the host protein of the primary antibody used in the immunohistochemical or the immunochemical detection process.

11. The control target array of claim 1, further comprising an imaging reference loading dot.

12. The control target array of claim 11, wherein the imaging reference loading dot comprises at least one:
 a black reference target comprising carbon dust;
 a white reference target, wherein the white reference target comprises a metal oxide or a metal sulfate; or
 a clear reference target, wherein the clear reference target comprises a non-reactive protein to any immunohistochemical or immunochemical reagents.

13. The control target array of claim 11, wherein the imaging reference loading dot comprises:
 an anhydride-based epoxy for a white reference target and a black reference target; and
 a protein from the equine family of mammals for a clear reference target.

14. The control target array of claim 1, further comprising an antigen retrieval monitor loading dot configured to monitor a degree of antigen retrieval in the immunohistochemical or the immunochemical detection process.

15. The control target array of claim 14, wherein the antigen retrieval monitor loading dot comprises a carrier protein or submicron bead comprising:
 host proteins covalently attached for defining a 3D particle; and
 a fixative under or over the host proteins.

16. The control target array of claim 1, further comprising a paraffin coating over the first plurality of control targets.

17. A method for immunohistochemical staining, the method comprising:
subjecting a slide and a control target array to a same fixation removal process to expose antigen sites in a tissue section on the slide and to expose control targets on the control target array;
staining the tissue section and the control targets, wherein the staining comprising: applying a primary antibody to the slide, applying a secondary antibody conjugated with a moiety to the slide; and applying stain reagents that produce color in a presence of the moiety to indicate a presence of a targeted antigen.

18. The method according to claim 17, wherein the control target array is on the slide.

19. The method according to claim 17, wherein the control target array is configured to:
 indicate an error and performance measure of intermediate steps during the immunohistochemical staining process, and
 provide a reference for qualitatively or quantitatively determining a color and antigen density of the stained tissue or cells.

20. A method for immunohistochemical staining, the method comprising:
 subjecting a slide and a control target array to a same fixation removal process to expose antigen sites in a tissue section on the slide and to expose control targets on the control target array;
 staining the tissue section and the control targets, wherein the staining comprising:
  applying one or more primary antibodies conjugated with a moiety to the slide; and
  applying stain reagents that produce color in a presence of the moiety to indicate a presence of a targeted antigen.

* * * * *